(12) United States Patent
Walke et al.

(10) Patent No.: US 9,125,620 B2
(45) Date of Patent: Sep. 8, 2015

(54) METHOD AND DEVICE FOR MOBILE TRAINING DATA ACQUISITION AND ANALYSIS OF STRENGTH TRAINING

(71) Applicants: Fabian Walke, Darmstadt (DE); Hauke Radtki, Darmstadt (DE)

(72) Inventors: Fabian Walke, Darmstadt (DE); Hauke Radtki, Darmstadt (DE)

(73) Assignee: Fablan Walke, Darmstadt (DE)

( * ) Notice: Subject to any disclaimer, the term of this patent is extended or adjusted under 35 U.S.C. 154(b) by 0 days.

(21) Appl. No.: 14/365,120

(22) PCT Filed: Dec. 14, 2012

(86) PCT No.: PCT/EP2012/075660
§ 371 (c)(1),
(2) Date: Jun. 13, 2014

(87) PCT Pub. No.: WO2013/087902
PCT Pub. Date: Jun. 20, 2013

(65) Prior Publication Data
US 2014/0336947 A1 Nov. 13, 2014

(30) Foreign Application Priority Data
Dec. 15, 2011 (DE) .......................... 10 2011 121 259

(51) Int. Cl.
*G01V 1/40* (2006.01)
*A61B 5/00* (2006.01)
(Continued)

(52) U.S. Cl.
CPC ............... *A61B 5/486* (2013.01); *A61B 5/0004* (2013.01); *A61B 5/0022* (2013.01); *A61B 5/1121* (2013.01); *A61B 5/1122* (2013.01); *A61B 5/1125* (2013.01); *A61B 5/1126* (2013.01); *A61B 5/224* (2013.01); *A61B 5/6801* (2013.01);
(Continued)

(58) Field of Classification Search
CPC .... G06F 3/011; A61B 5/1118; A61B 5/1123; A61B 5/11
USPC .................................................. 702/160–163
See application file for complete search history.

(56) References Cited

U.S. PATENT DOCUMENTS 4,660,829 A   4/1987  Whiteneir et al.
5,676,157 A  10/1997  Kramer
(Continued)

FOREIGN PATENT DOCUMENTS

CA    1148186 A1   6/1983
DE    4222373 A1   1/1994
(Continued)

OTHER PUBLICATIONS

Translation of International Preliminary Report on Patentability for PCT/EP2012/075660.*

*Primary Examiner* — Phuong Huynh
(74) *Attorney, Agent, or Firm* — Joyce von Natzmer; Agris & von Natzmer LLP

(57) ABSTRACT

The invention relates to the field of mobile training data acquisition in sport, particularly in strength training, body building, fitness sports and rehabilitation, as well as the analysis of said training data. The invention involves a method and a mobile device (1) for precise acquisition of multiple training data. The multiple training data includes, for example, the time-path curve of the force application point of the training load, the mechanical work and the tension duration of eccentric and concentric muscle length changes and isometric muscle contractions. An analysis of the training data is based on a training model (25).

19 Claims, 12 Drawing Sheets

(51) Int. Cl.
*A61B 5/11* (2006.01)
*A61B 5/22* (2006.01)
*G06F 11/00* (2006.01)

(52) U.S. Cl.
CPC ............... *A61B 5/6898* (2013.01); *A61B 5/742* (2013.01); *A61B 5/7405* (2013.01); *A61B 5/7455* (2013.01); *A61B 5/7475* (2013.01); *A61B 5/1123* (2013.01); *A61B 5/681* (2013.01); *A61B 5/725* (2013.01); *A61B 5/7242* (2013.01); *A61B 5/7267* (2013.01); *A61B 2562/0219* (2013.01)

(56) References Cited

U.S. PATENT DOCUMENTS

| | | |
|---|---|---|
| 5,807,284 A | 9/1998 | Foxlin |
| 6,280,361 B1 | 8/2001 | Harvey et al. |
| 6,514,219 B1 | 2/2003 | Guimond et al. |
| 6,796,925 B2 | 9/2004 | Martinez et al. |
| 6,820,025 B2 | 11/2004 | Bachmann et al. |
| 6,834,436 B2 | 12/2004 | Townsend et al. |
| 2005/0046576 A1* | 3/2005 | Julian et al. ................ 340/573.1 |
| 2007/0219059 A1 | 9/2007 | Schwartz et al. |
| 2008/0090703 A1 | 4/2008 | Rosenberg |
| 2008/0204225 A1* | 8/2008 | Kitchen .................... 340/539.22 |
| 2009/0009320 A1 | 1/2009 | O'Connor et al. |
| 2009/0069722 A1 | 3/2009 | Flaction et al. |
| 2009/0281462 A1 | 11/2009 | Heliot et al. |
| 2011/0046519 A1 | 2/2011 | Raheman |
| 2011/0082394 A1 | 4/2011 | Chiu et al. |
| 2011/0207581 A1 | 8/2011 | Flaction et al. |

FOREIGN PATENT DOCUMENTS

| | | |
|---|---|---|
| DE | 19830359 A1 | 1/2000 |
| DE | 10029459 A1 | 9/2001 |
| DE | 102006047099 A1 | 4/2008 |
| EP | 1688746 A2 | 8/2006 |
| EP | 1834583 B1 | 9/2007 |
| JP | 2007209636 A | 8/2007 |
| WO | 9426359 A1 | 11/1994 |
| WO | 0169180 A1 | 9/2001 |
| WO | 2009/013679 A2 | 1/2009 |
| WO | WO 2009/013679 A2 * | 1/2009 |

* cited by examiner

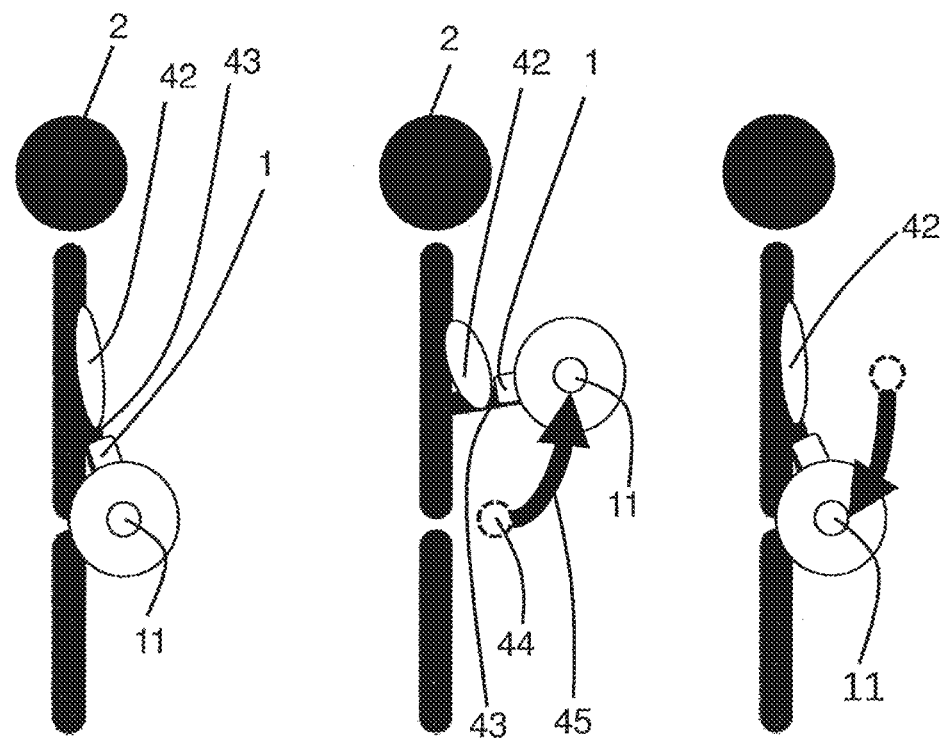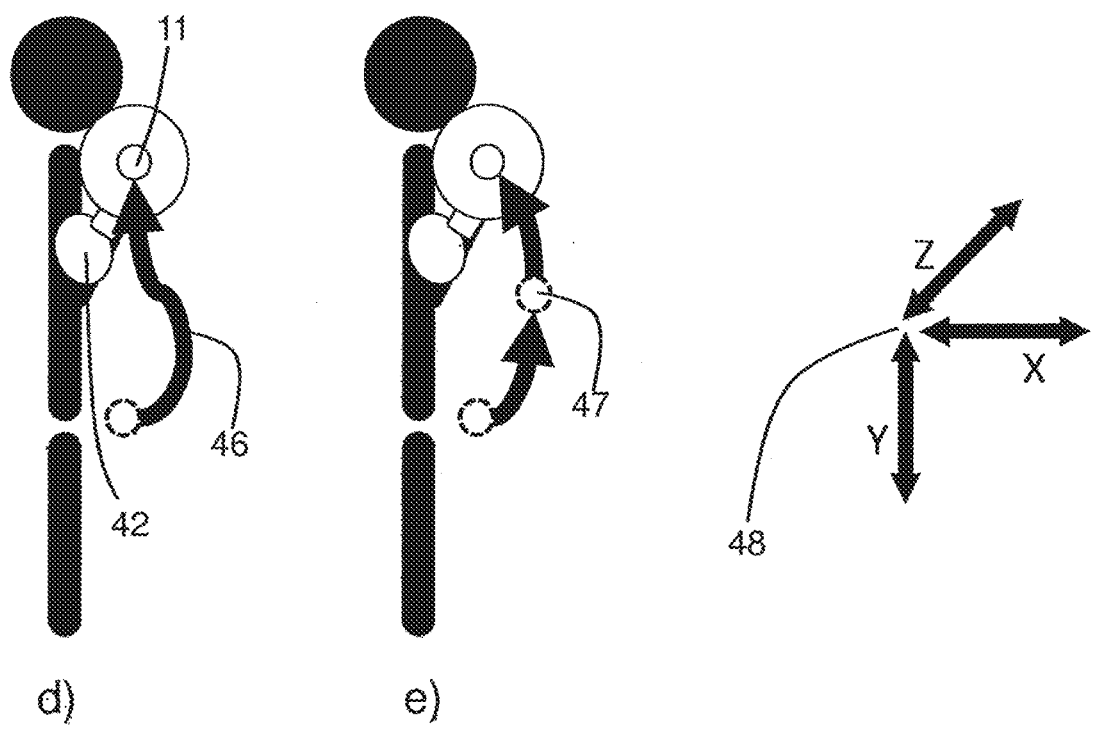
FIG. 6

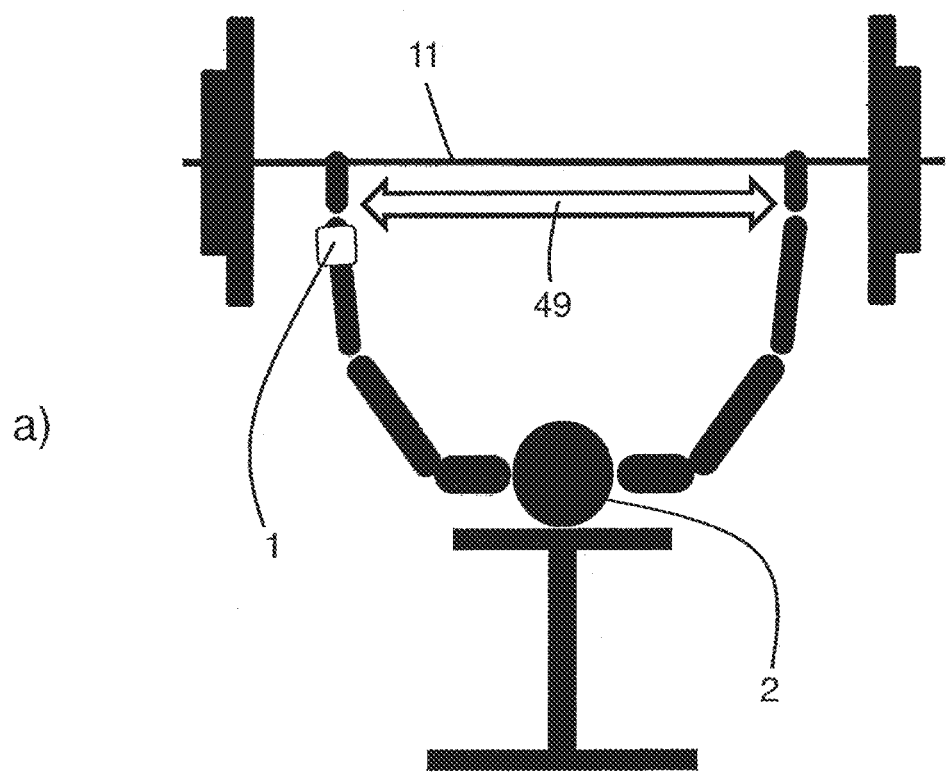
a)
FIG. 7
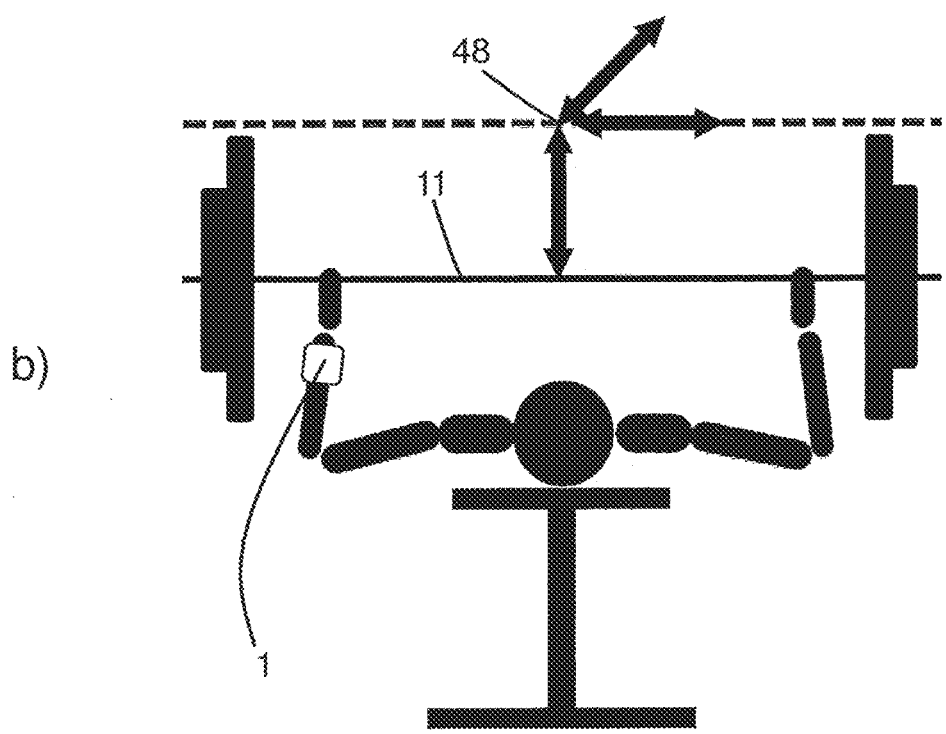
b)

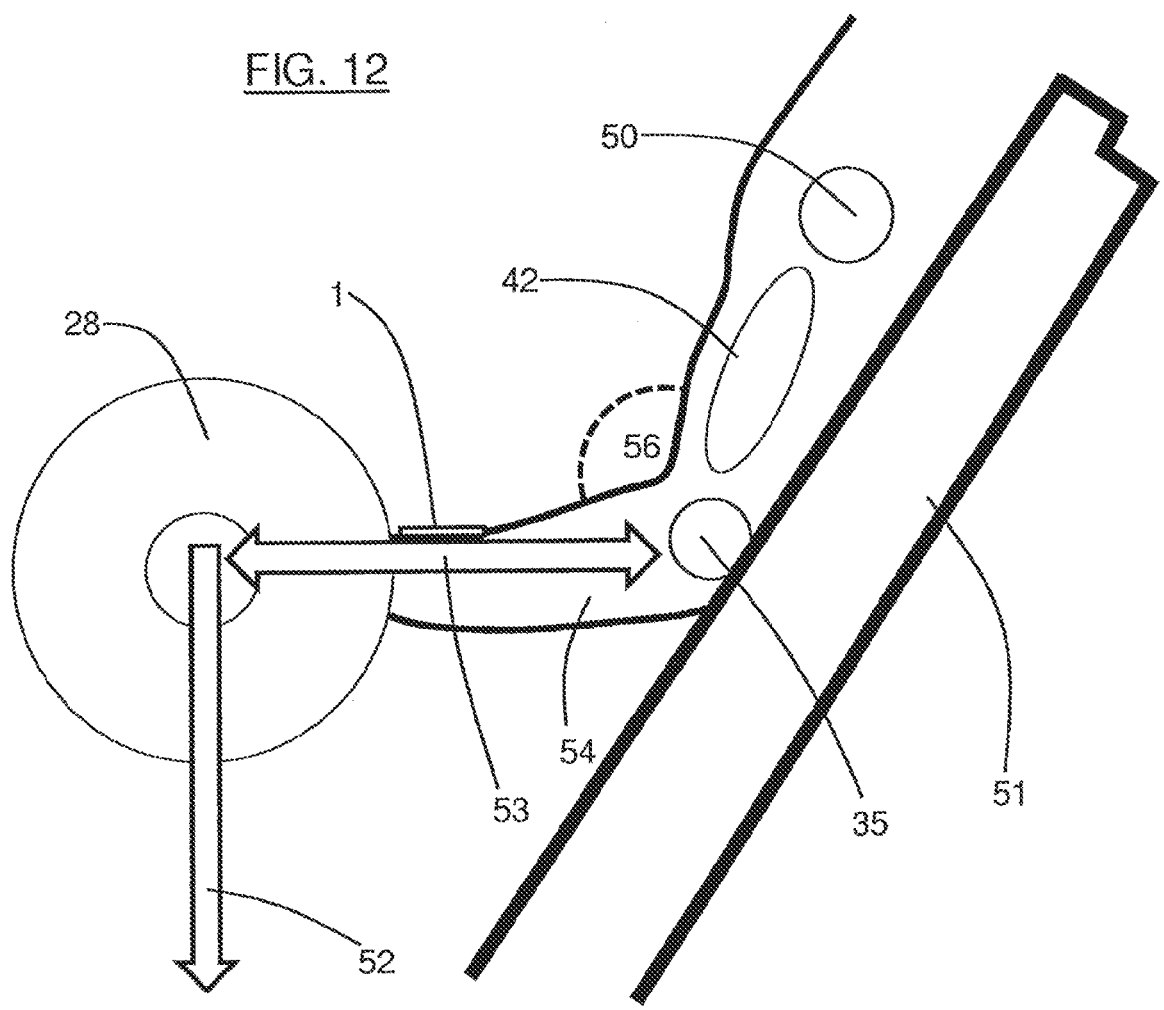

METHOD AND DEVICE FOR MOBILE TRAINING DATA ACQUISITION AND ANALYSIS OF STRENGTH TRAINING

This is the U.S. national stage of International application PCT/EP2012/075660, filed Dec. 14, 2012 designating the United States and claiming priority to German application DE 10 2011 121 259.4, filed Dec. 15, 2011.

In fitness studios, weight rooms, health centers, physiotherapy practices or rehabilitation institutions, athletes/patients are provided with a large number of training utensils, which, inter alia, can be subdivided into training with dumbbells, barbells, own body weight, stationary machines/equipment, cable machines and cardio-equipment. Due to the low opposing force of the cardio-equipment, endurance training is carried out; by way of example, the pulse is acquired and the calorie consumption is calculated. By contrast, in strength training work is undertaken against higher loads and e.g. dumbbells, barbells, machines, cable machines or the own body weight are used as opposing force. The term strength training can also include bodybuilding, muscle strength training and, in parts, fitness training. The goal of strength training, particularly in the case of fitness-oriented strength training, is to increase the maximum strength and the muscle increase connected therewith. The previous inventions in strength training usually acquire the training data on large, stationary machines, for example by means of cable pull sensors. Other mobile devices measure parameters such as e.g. change in angle, force, speed or power, which are applied for direct assessment or optimization of the performance. In the following text, the previous inventions and options for training data acquisition and the analysis of this training data are explained.

EP 1834583B1 and US 20110207581A1 describe an invention which uses accelerometers to calculate parameters such as e.g. muscular strength, speed, power, height of the jump in the case of countermovement jumps, reactivity, muscular elasticity property or coordination by carrying out test movements in order to acquire directly the training state or the performance level of the athlete and to optimize the training by calculations on the basis of the acceleration values. Here, this involves a limited number of tests, such as e.g. the acquisition of the jump height in the case of a countermovement jump. The training optimizations are based on acceleration data or the aforementioned muscular parameters. A personalized "muscular profile" (US 20110207581A1, page 3, [0043]) is based on strength, power and speed curves. "Personalized power curves" (US 20110207581A1, page 3, [0044]) render it possible to set the training load in order to cause specific adaptations by selected training regions (e.g. muscle hypertrophy). This form of determining the maximum strength (repetition maximum, abbreviated RM) sets the training intensity load parameter, i.e. the training load, as a result of which the training is to be optimized.

U.S. Pat. No. 6,280,361B1 describes an invention which generates tension forces with the desired resistive force in several cables by means of a controlling structure. Using this invention, any form of training exercise can be carried out with a resistive force, even in a gravity-free environment. This invention enables stationary strength training.

WO 9426359 describes an invention, which acquires the movement of a joint by means of an inclination sensor. By means of this invention, it is possible to store individual predetermined rehabilitation programs and to acquire the fulfillment of the rehabilitation program on the basis of angle measurements in the joints. This invention is characterized in that it undertakes calculations by means of an inclination sensor.

US 0250286A1 describes an invention for monitoring movements of a subject by means of a multiplicity of sensor elements attached to movable body segments of a subject. By means of this invention, it is possible to register a multiplicity of movements during acute and chronic lifting tasks in order to determine and correct disease of the lumbar vertebral column and repetitive load injuries.

JP 2007209636 describes an invention, which enables an individual undertaking training to acquire measurement variables from a training repetition, such as time or frequency, by means of an accelerometer and to transfer said measurement variables to a computer.

U.S. Pat. No. 6,796,925B2 describes an invention which can measure the movement repetitions of training exercises of an athlete by means of a proximity sensor. By means of this invention, it is possible to acquire the number of movement repetitions in certain exercises.

US 20080090703A1 describes an invention for automatically counting repetitions and orchestrating exercises. This invention enables access to a predetermined training program from a portable computer such as e.g. a smartphone or PDA. The movement repetitions are added, like in the invention U.S. Pat. No. 6,796,925B2. To this end, two different modules are necessary. Firstly, a "portable computer device", such as e.g. a smartphone and an external transmitter with accelerometer, which transmits the measurement data wirelessly to the portable computer.

EP 1688746A2 describes an invention which measures human body movements. These body movements are acquired by means of an accelerometer.

WO 0169180A1 describes an invention, which renders it possible to measure the speed and distance during a running motion, for example during endurance training.

U.S. Pat. No. 6,820,025B2 describes an invention for identifying movement on a rigid body connected by hinges. This invention can determine the position of a sensor in space.

US 005807284A describes an invention for tracking the human head or bodies of similar size. By way of example, this invention serves to track head movements in virtual reality applications.

DE 10029459A1 describes an invention for acquiring the position and/or movement of an object and/or living being and parts of this apparatus. By way of example, this invention is suitable for determining the position of a match ball on an association football field in order, for example, to determine whether the ball was positioned behind the goal line in the case of a shot on goal.

DE 10029459A1 describes an invention which can recognize, track, display and identify the repeating movements of swimmers. The application of the invention relates to swimming-specific movement patterns, two movement axes and acceleration data.

CA 1148186 describes an invention, which enables tennis players to learn the controlled bending of the wrist. "It is therefore the primary object of this invention to provide means whereby a player can be automatically informed of errors, so that he can learn to avoid them." (CA 1148186, pages 1-2). In order to determine the bend of the wrist, use is made of several bands and cables, and also an external recording device and sensor unit. The invention is not situated in a single closed device. The external recording device stores the number and frequency of the bends of the wrist.

DE 4222373A1 describes an invention for measuring path and speed of athletes such as e.g. skiers, surfers, sailors or cyclists. Use is made of an accelerometer for calculating the path and the speed.

DE 19830359A2 describes an invention for determining spatial positioning and movement of body parts and bodies by means of a combination of inertial orientation pickups and position acquisition sensor systems. By way of example, this invention could be used to determine the position of a body segment in space or in a partial coordinate system.

US 005676157A describes an invention for determining kinematically restricted multi-hinged structures. This invention renders it possible to determine the spatial position and orientation of body segments.

DE 102006047099A1 describes an invention for collecting and preparing training data in a fitness studio. This invention enables an acquisition of training data on stationary training equipment in the form of force, movement and repetition information and the preparation of the data for monitoring the training.

US 20070219059A1 describes an invention for continuously monitoring exercises and the real-time analysis thereof. As a result of this invention, it is possible to monitor body noises, body signs, vital functions, movements and machine settings continuously and automatically. This invention is designed specifically for heart-lung monitoring of an athlete during a training program in order to ensure the safety when carrying out exercises, particularly in the case of rehabilitation patients.

U.S. Pat. No. 4,660,829 describes an invention, which renders it possible to acquire movements of two body segments, e.g. the wrist and the forearm, in sports such as e.g. tennis. Two separate modules are used to acquire these movements.

US 20110082394A1 describes an invention for monitoring sports-related fitness by estimating the muscle strength and the common strength of extremities, said invention consisting of a sensor module and a force/path detection module for classifying movement series in relation to the muscle strength and the common strength of the limbs. By way of example, this invention can be used to identify/classify movements, which, for example, are carried out in the upper and lower limbs.

U.S. Pat. No. 6,514,219B1 describes an invention for automatic biomechanical analysis and identification and correction of posture deviations. By means of optical markers at various body joints, this invention renders it possible to detect said body joints in space and to undertake analyses.

U.S. Pat. No. 6,834,436B2 describes an invention in order to be able to distinguish a lying, seated or standing position of the human body. Furthermore, this invention can be used to determine too much or too little activity of joints or movements.

In order to analyze training data, use has until now been made in sports sciences, particularly in team sports and in endurance training, of mathematical and statistical models or unconventional modeling paradigms. By way of example, these models serve in predicting competition performance (e.g. in swimming) or in analyzing tactical interactions in team sports (e.g. in association football). Until now, previous models, which are intended to serve for analysis and predictions of training effects (performance), have a low model quality and prediction power, greatly simplify the interaction of training load and performance (e.g. one input variable and one output variable) or do not allow causal interpretations of the results. Furthermore, these are restricted in terms of their temporal depth, linked to a multiplicity of conditions (e.g. only advanced athletes) and the results are not evaluated by algorithm, i.e. they do not result in specific training recommendations. In order to deduce training recommendations from the results of such a model, there was always need for experts (e.g. trainers), who can interpret the difficult to understand connection between training load and performance.

When looking at the listed inventions, it becomes clear that, until now, no invention has been developed for strength training, which renders it possible to capture a multiplicity of relevant training data, in all strength-training exercises, with all training utensils, in a precise manner, without relying on fixedly predetermined training programs, smartphones and/or electronic stationary strength training instruments. When looking at the models for training data analysis, it becomes clear that, until now, a continuous analysis of training data in strength training is lacking; i.e., there is no model that can derive specific training recommendations from the analyses (control of the strength training) and predict the performance of the user in strength training with a high model quality. In the listed inventions, a generic method for training data acquisition comprises the following steps: affixing a mobile device to a body segment; determining sensor values in movement patterns by means of said mobile device; calculating training data from said sensor values using said mobile device; storing said training data in a first storage unit in said mobile device; transmitting said training data from said mobile device to a computer via a data interface. In the listed inventions, a generic device for training data acquisition contains: a housing; a sensor for determining sensor values; a processor for calculating training data; a first storage unit for storing said training data; a data interface for transmitting said training data to a computer.

In order to be able to acquire precisely a multiplicity of relevant training data, in all strength-training exercises, with all training utensils, a user requires a selection of strength-training exercises and training utensils in an invention in order to be able to calculate precisely the aforementioned relevant training data since the measurement values vary greatly depending on strength-training exercise and selected training utensil. Furthermore, in order to obtain valid training data, users require a method, which can determine the position of the force contact point of the training load in space. When determining sensor values, this method can only be really precise if the mathematical structure and the measurement errors are already known in the respectively selected strength-training exercises with a training utensil and the associated set movement patterns. In order to provide algorithm-based training recommendations in strength training (control of the strength training) and in order to be able to predict the performance of a user in strength training, the one-time acquisition of training data in a training unit is insufficient. Training data have to be acquired and analyzed over a relatively long period of time (continuously in various training process planes).

By improving a generic method and a generic device, it is an object of the invention to offer a user the option in strength training of being able to precisely acquire relevant training data in all strength-training exercises, with every available training utensil, and to analyze these training data and to control the strength training on the basis of a multiplicity of training data and to be able to calculate predictions of the performance.

In accordance with a first aspect of the invention, this object is achieved by a method for precise, mobile acquisition of training data, consisting of the following steps: selecting a strength-training exercise with a set movement pattern and a training utensil, from N strength-training exercises and M training utensils by means of a mobile device; recalling predetermined movement data, consisting of the characteristic variables of set movement patterns of one said strength-training exercise X using one said training utensil Y from a second storage unit in said mobile device; determining raw sensor values using said mobile device in said set movement patterns of said strength-training exercise X using said training utensil Y, consisting of acceleration and angular speed values; calculating reworked measurement values using said mobile device depending on said predetermined movement data and said raw sensor values; precisely calculating multiple training data using said mobile device, on the basis of said reworked measurement values.

It was found that the significance during the analysis of training data can be increased if a multiplicity of training data are acquired, which is why the acquired training data are referred to as "multiple training data", although these can also contain a single training data parameter. The term "precise" is defined in such a way that the movement patterns are predetermined by the selection of the strength-training exercises and training utensils and, as a result thereof, the mathematical structure and the measurement errors are known. These said predetermined movement patterns are located on the second storage unit in the mobile device and are processed together with the raw sensor data. Inventions that do not explicitly contain modeling of the strength-training exercises with said training utensils have less precise calculations since movement patterns and sensor values are not known in advance. The term "relevant" is defined in such a way that said multiple training data are necessary for the training progress of the user. Training data from other inventions, such as e.g. information relating to the distance run, would be unusable for analysis of strength training.

A second aspect of the invention relates to a device for precise, mobile training data acquisition, consisting of: the second storage unit on which the predetermined movement data are stored, which movement data consist of the characteristic variables of set movement patterns of N strength-training exercises using a training utensil Y, and are recalled from the processor; an accelerometer and rate sensor for determining acceleration and/or angular speed values, which are transmitted to the processor. This device is the mobile device of the method for precise, mobile training data acquisition. The mobile device can be embodied in the form of a wristwatch. Furthermore, the mobile device contains a wireless interface for wireless data interchange with at least one sensor module and/or at least one wireless station and/or any other devices. The wireless interface serves for wireless transmission of data. By way of example, it can be embodied as a 2.4 GHz wireless interface. The wireless station can for example serve for real-time data transmission, for example in a fitness studio. By way of example, the sensor module can correspond to a restricted embodiment variant of the mobile device. By way of example, the other devices can be human scales and/or smartphones and/or body composition analyzers. The mobile device contains an RFID unit, which is embodied as RFID reading unit and as RFID transmission unit; said RFID unit can communicate with RFID tags, which are attached to said training utensil and/or integrated in said training utensil and/or situated in the vicinity of said training utensil, and/or with external devices. By way of example, the training utensils can include "dumbbells", "barbells", "cable machines", "machines" or the "own body weight". By way of example, the external devices are turnstiles, by means of which e.g. check in/out into/from the fitness studio is carried out, and/or lockers, which can e.g. be opened or locked, and/or base stations, at which e.g. training data can be recalled. Furthermore, the mobile device contains a magnetometer for measuring the magnetic flux density vector. Moreover, the mobile device contains a user interface and/or a display unit and/or a vibration motor and/or a loudspeaker. By way of example, the user interface can be in the form of buttons/keys, which e.g. are situated on the outer edge of the mobile device. The display unit, for example in the form of a display, shows the user a graphical user interface. The display unit itself can be embodied as a user interface, for example in the form of a touchscreen. The raw sensor values and/or the reworked measurement values and/or the multiple training data can be stored on a first storage unit. The second storage unit contains the predetermined movement data. The first storage unit and/or the second storage unit can e.g. be configured as integrated flash module and/or as SD memory card. The sensors in the mobile device are the accelerometer, the rate sensor (gyroscope) and the magnetometer. The processor, inter alia, recalls the predetermined movement data from the second storage unit and obtains the raw sensor values from the sensors. The reworked measurement values are generated in an algorithm, depending on the raw sensor values and the predetermined movement data from the second storage unit. Furthermore, the mobile device contains a rechargeable battery, for example a lithium rechargeable battery. The mobile device contains an interface (also referred to as data interface), for example a USB interface, which is employed both for data transmission to a computer of the user and for supplying the mobile device with power.

Calculating reworked measurement values using the mobile device comprises at least one of the following steps:
  initially calibrating said mobile device in order to improve said calculation and/or extend said multiple training data;
  including said magnetic flux density vector in said raw sensor values;
  fusing said raw sensor values with said predetermined movement data;
  integrating said acceleration values twice;
  filtering sensor offsets.

Combining an accelerometer and a rate sensor, and fusing the raw sensor values and the predetermined movement data, for example by means of a Kalman filter/direction cosine matrix, allows the alignment of the mobile device in space (roll angle, pitch angle, yaw angle) to be calculated relative to the Earth. Calculating the alignment in the moved state by means of acceleration data only is not possible, since, in addition to the gravitational acceleration, further accelerations that cannot be separated occur. As a result of the known alignment, it is possible to transform the acceleration data from the local system (mobile device) into the global coordinate system. It is possible to determine accelerations in the global coordinate system. Only as a result of the conversion of the accelerations is it possible to calculate movement vectors and all variables resulting therefrom. With the aid of the set reference system, it is also possible to attach the mobile device at positions that rotate during the planned movement, even though the movement is in a straight line. As a result of a mathematical correction, the mobile device can also be situated away from the center point of the movement, i.e. the force contact point of the training load, if the respective distances are entered into the mobile device. The movement vector of the mobile device can be recorded by integrating the accelerations twice. A systemic offset as a result of drift of the accelerometer and the rate sensor over time can be eliminated by e.g. high-pass filters, particularly in the case of two-fold integration. Since the displacement/time profile of the force contact point of the training load is therefore known, it is possible e.g. to acquire the movement rhythm, the movement amplitude and the movement direction.

In order to further increase the accuracy of the method, the preliminarily calculated position of the mobile device, specifically the movement thereof in space, is subjected to further plausibility tests. Here, information in relation to the human skeletal system, for example, is included.

On the basis of said raw sensor values, said multiple training data contain at least one of the following items of information:
- precise displacement/time profile of the force contact point of the training load along the X-axis and/or Y-axis and/or Z-axis;
- time under tension of eccentric muscle length changes and/or concentric muscle length changes and/or isometric muscle contractions;
- number of movement repetitions;
- mechanical work;
- rotational work;
- muscle load;
- torque;
- force;
- impulse;
- physical effect;
- grip width;
- grip variant;
- foot position;
- initial angle of a superior joint;
- muscle length state;
- level of exertion;
- type of movement in a joint;
- intensity technique applied in a training set;
- training method.

Individual items of training data of the multiple training data can also be acquired and/or processed further with time dependence, such as e.g. the time-dependent processing of the torque (torque/time profile). For other training data, such as e.g. the displacement/time profile of the force contact point of the training load along the X-axis and/or Y-axis and/or Z-axis, it may be sufficient for merely individual value ranges, such as e.g. the displacement profile, to be acquired.

In order to improve the calculation and/or extend the multiple training data, a calibration is carried out prior to the start of the movement pattern, as a result of which the location and position of said mobile device in space is calculated. Furthermore, the initial position of body segments in strength-training exercises is established by the calibration and additional training data are calculated, such as e.g. the initial angle of a superior joint, for example the shoulder joint in the case of a strength-training exercise in which there is bending and/or stretching in the elbow joint, and/or a gripping width, for example on a barbell, and/or the position of one foot or of both feet, for example in the case of strength-training exercises with bending and/or stretching of the knee. The gripping width can, for example, be calculated by an angle of the forearm in relation to the training utensil (for example "barbell"). To this end, it is necessary for a selected distance of the hands and the associated angle of the forearm to be known once. These distances can, in the case of a predetermined angle of the forearm, be entered manually by the user by means of the user interface and/or the display unit. Following this, the grip width can be calculated automatically, without manual specifications having to be provided a second time. The same procedure relates to the foot position and an angle of the shank in relation to the training utensil. Moreover, it is possible for the grip variant (e.g. prone grip, supine grip, hammer grip, palm grip, pinch grip, EZ grip) to be selected by means of the user interface and/or display unit and/or for the grip variant to be acquired in an automated fashion on the basis of the raw sensor values.

Further training data are acquired, which contain at least one of the following items of information:
- training load;
- type of training utensil;
- type of strength-training exercise;
- modified application of force on the contact point of the training load when selecting the cable machine and/or machine training utensil;
- intended speed;
- rest times between movement repetitions and/or training sets and/or strength-training exercises and/or training units and/or micro-cycles and/or meso-cycles and/or macro-cycles;
- number of training sets and/or strength-training exercises and/or training units and/or micro-cycles and/or meso-cycles and/or macro-cycles;
- duration of movement repetitions and/or training sets and/or strength-training exercises and/or training units and/or micro-cycles and/or meso-cycles and/or macro-cycles;
- date and time of a training unit;
- subjective current form;
- sequence of strength-training exercises.

The method contains a user selecting a training load and/or the training utensil and/or the strength-training exercise in an automated manner by means of an RFID unit and RFID tag and/or selecting it in a manual manner by means of the user interface and/or the display unit, and/or the strength-training exercise being acquired automatically, proceeding from the raw sensor values. Here, the "acquisition" is an option for said selection of said strength-training exercise X. Here, the selection of the training load relates to a subset of the multiple training data. The automated selection by means of the RFID unit is brought about by means of an RFID tag which is attached to the training utensil, e.g. a barbell, and/or which is integrated into the training utensil and/or situated in the vicinity of the training utensil. The RFID tag transmits "training load", "type of training utensil" and optionally also "type of strength-training exercise" information to the mobile device. In the example of the "barbell" training utensil, the training load emerges from the sum of the mass of the barbell and the weight disks attached to the barbell. The mobile device is configured to sum the mass of the training utensil and the weight disks and to combine this to form an item of training load information. The same procedure is called for in the case of the dumbbell training utensil. If this is a compact dumbbell, in which the number of weight disks cannot be changed, there is no need to sum up the training weights.

This information relating to what strength-training exercise is carried out is already predetermined when selecting the "machine" training utensil in the case of most machines since machines fixedly predetermine the movement pattern in strength training. As a result, the RFID tag can also transmit the "type of strength-training exercise" information to the mobile device. In the case of the barbell, dumbbell, cable machine and body strength training utensils, the movement patterns are only fixedly predetermined in combination with a strength-training exercise. Accordingly, different strength-training exercises can be carried out using one training utensil. When selecting the "dumbbell", "barbell", "cable machine" and "machine/equipment" training utensils, predetermined movement patterns relate to the strength-training exercise being carried out correctly using these training utensils. Naturally, as a result of the predetermined movement patterns in the strength-training exercise X, the user is not restricted in his movement options with the dumbbell, barbell, cable machine and body strength training utensils.

If the selection is undertaken manually by means of the user interface and/or the display unit, or if this is the "machine" training utensil with an RFID tag, the predetermined movement data of a strength-training exercise X using a training utensil Y, situated in said second storage unit, are recalled directly by the processor and continuously processed with the raw sensor values. If the user does not select a strength-training exercise prior to the movement pattern, it is possible to acquire a strength-training exercise automatically, proceeding from the raw sensor values.

Within training practice, the scope of the training is, for reasons of simplicity, calculated from the product of the number of movement repetitions and training load. Naturally, this method of calculation does not provide information about the actual mechanical work done. The mechanical work is calculated from the product of force and displacement. Since all strength-training exercises are body segment movements by rotations about joint axes, the rotational work, which emerges from the product of torque and rotational angle, is also calculated. The distances required for calculating the torque (e.g. the distance between force contact point of the training load and the rotational axis/joint, i.e. the lever) can be entered into the mobile device by means of the user interface and/or the display unit.

When the cable machine and/or machine training utensil is selected, the modified application of force on the contact point of the training load can be calculated in the case of gear-reduced training utensils (weight over a pulley or the like) if a gear reduction factor is manually entered by the user using the user interface and/or the display unit and/or if the gear reduction factor for a specific cable machine and/or machine type is already stored on the mobile device.

In relation to the change in length of the muscular system, there are three types of muscle work and three forms of muscle contractions: dynamic-positive, dynamic-negative and static muscle work, as well as concentric and eccentric muscle length changes and isometric muscle contractions. When statically holding a training utensil (isometric muscle contraction), no work is performed in the physical sense, but the muscle continues to consume energy. Thus, it does not suffice to calculate the extent of the training only by the mechanical work. A further measurement variable has to be added. This is the so-called time under tension (abbreviated TUT), which is often also referred to as "physiological work" or "tension time" in the literature. The time under tension of the muscles is calculated in this case not only during isometric contractions (static holding work), but also during eccentric and concentric muscle length changes, i.e. in the case of dynamic-positive and dynamic-negative muscle work.

In order to be able to calculate the time under tension of a muscular system in a strength-training exercise, information with respect to the anatomy of the human skeletal system and the functions of the muscular system already has to be provided. In joints, muscles can, for example, have the function of internal and external rotation, translation, abduction and adduction, extension and flexion, supination and pronation, and also anteversion and retroversion. Here, in strength-training exercises, there is a so-called target muscular system, to which mainly the main load is applied in the respective training exercise (e.g. "m. pectoralis major" in the "bench press" training exercise), a supporting muscular system (e.g. "m. triceps brachii" and "m. deltoideus clavicularis" in the "bench press" training exercise) and a stabilizing muscular system, usually the antagonistic contracting muscular system (e.g. "m. biceps brachii" in the "bench press" training exercise). The muscles to which load is applied in strength training are stored in the second storage unit and are automatically assigned to the respectively selected strength-training exercises. In order to be able to weight the load of one or more muscles (the muscle loads) in strength-training exercises, research results of electromyographic examinations are included, in addition to the anatomical information, in the weighting of muscle loads in strength-training exercises.

The movement rhythm of static, dynamic-positive and dynamic-negative muscle work is also referred to as cadence in training practice. In some training methods, this cadence is deliberately drawn out and extremely slow movements are carried out, for example in the dynamic-negative phase. In training practice, the user finds it difficult, without support, to maintain precise prescriptions of cadences, for example four seconds dynamic-negative, two seconds static, four seconds dynamic-positive muscle work. Furthermore, in joints of the human body, there is a work angle, in which there is a maximum distance between the line of action of the force contact point of the training load and the rotational axis/joint and hence in which a larger torque is generated for the same amount of force. This angle range around the maximum torque is also referred to as "optimum work angle" in sports sciences. By way of example, this is 60°-120° in the elbow joint and 110°-120° internal angle when extending the knee. In training practice, this optimum work angle can only be maintained with difficulty by the user without support. In this optimum work angle, in which the greatest amount of torque is generated, muscles can be situated in different length states. In sports sciences, three muscle length states are differentiated from a classification point of view: a stretched muscle length state, a contracted muscle length state and a middling muscle length state. In the stretched length state, the muscle is stretched, in the contracted length state, it is pulled together and in the middling length state said muscle is between the stretched and the pulled-together length state. Naturally, the transitions between the muscle length states are continuous. What length state muscle is situated in depends on the initial angle of a superior joint, for example, the shoulder joint in the case of a strength-training exercise in which there is bending and/or stretching in the elbow joint. This initial angle of a superior joint can be acquired by said initial calibration of the mobile device, as a result of which the muscle length state is also acquired.

As already described above, the invention does not restrict the user in the movement options in strength-training exercises. Accordingly, the user can also undertake deviations from an ideal line of the movement of a strength-training exercise X using a training utensil Y. These deviations are acquired and can relate to the movement amplitude and/or the movement direction. The movement amplitude is movement, joint and muscle specific and varies from user to user, which is why there can optionally be an initial calibration using the mobile device, in which the full movement amplitude in the strength-training exercise is employed.

The method contains optical and/or acoustic and/or haptic signals being provided to said user by means of said mobile device for the purposes of support when carrying out the predetermined movement pattern, wherein said signals contain information about e.g. the rhythm and/or the amplitude and/or the direction of the predetermined movement pattern. By way of example, the user can more easily maintain the cadence (movement rhythm), which e.g. is predetermined by a training method and/or training plan, and/or the movement direction and/or the movement amplitude of a predetermined movement pattern of a strength-training exercise and/or the optimum work angle in a joint as a result of the optical and/or acoustic and/or haptic signals.

Furthermore, it is possible to acquire the date and the time of a training unit. Furthermore, it is possible to acquire pause times between movement repetitions, training sets, strength-training exercises, training units, micro-, meso- and/or micro-cycles. Moreover, it is possible to acquire the duration of movement repetitions and/or training sets and/or strength-training exercises and/or training units and/or micro-cycles and/or meso-cycles and/or micro-cycles. By way of example, a micro-cycle can comprise a week, a meso-cycle can comprise ten weeks and a macro-cycle can comprise thirty weeks, during which e.g. several training units were completed. Furthermore, it is possible to acquire the number of movement repetitions and/or training sets and/or strength-training exercise and/or training units and/or micro-cycles and/or meso-cycles and/or micro-cycles. It is also possible to acquire the sequence of strength-training exercises. Moreover, in said mobile device, it is possible to enter an intended speed manually by means of the user interface and/or the display unit if said speed does not correspond to the actual speed. By way of example, this may be the case if, as a result of a very high training load, the movement is carried out very slowly, but, in actual fact, work is undertaken with the maximum speed against the training load. Moreover, an applied intensity technique (e.g. reduction set, partial repetitions, supersets, negative set, etc.) can be selected in the mobile device after each training set. These intensity techniques are already in the multiple training data as implicit information, but can be stored explicitly by the user during the training unit. Furthermore, the mobile device can remind a user of a training unit by means of optical and/or acoustic and/or haptic signals. This reminder can be set individually, for example by means of the user interface and/or display unit and/or wireless interface and/or interface.

The method contains additional raw sensor values being transmitted from at least one said sensor module to said mobile device via the wireless interface. The sensor module, which, for example, corresponds to a restricted embodiment variant of the mobile device, e.g. without the user interface, the display unit and the RFID unit, enables the acquisition of the additional raw sensor values and the wireless transmission of the additional raw sensor values to the mobile device. The additional raw sensor values can also be preprocessed in the sensor module prior to the transmission to the mobile device. As a result of the sensor module, there is no need to reposition the mobile device when changing to specific strength-training exercises (e.g. from a leg exercise to an upper body exercise). By way of example, the mobile device is situated on the wrist/forearm and the sensor module is on the ankle joint of the user. By way of example, the mobile device positioned on the wrist/forearm is configured in combination with the sensor module positioned on the ankle joint, which can calculate said multiple training data in all strength-training exercises, with all training utensils, without having to reposition the mobile device and/or the sensor module depending on the strength-training exercise X with the training utensil Y. Nevertheless, repositioning to other body segments (e.g. hip, thigh, upper arm, wrist/forearm, chest) and/or to the training utensil itself (e.g. in the case of pure wrist joint extensions and/or bends) can optionally be undertaken; and this is communicated between the user and the mobile device by means of e.g. the user interface and/or display unit. This arrangement can be complemented by a chest belt, which is positioned on the chest of the user and on which the sensor module is attached and/or integrated. This chest belt can be configured to acquire the pulse.

Furthermore, the method contains said multiple training data and/or said reworked measurement values and/or said raw sensor values and/or said further training data being transmitted to the first storage unit in said mobile device and/or transmitted to a computer and/or the wireless station via the interface and/or the wireless interface and transmitted to a training data server via the Internet and/or transmitted to a computer of an external user via the Internet and/or a direct connection. The user logs onto said training data server with a user profile over the Internet. On said training data server, the user enters personal user data, for example training experience in a specific time unit, performance values, age, sex, prior illnesses, further athletic activities, habitual bodily exercise, energy supply, temporal and motivational aspects, previously used training methods and training contents, date of the last carried out training unit, personal training goals, body weight, body fat proportion, total fat-free muscle mass, local fat-free muscle mass, body fat mass. By way of example, the user can transmit the multiple training data and/or the reworked measurement values and/or the raw sensor values and/or the further training data to the training data server by his computer and via the Internet and has access on the training data server to already transmitted said multiple training data and/or said reworked measurement values and/or said raw sensor values and/or said further training data. By way of example, the wireless station can be placed in a fitness studio and can serve for real-time data transmission. The external user can, for example, be a trainer, physiotherapist or medical practitioner, wherein the latter can access the training data server and receives the multiple training data and/or said reworked measurement values and/or said raw sensor values and/or said further training data transmitted in real-time to his computer by the wireless station. By means of his computer, the external user can control the mobile device and/or undertake settings, i.e. for example store movement patterns of specific movement repetitions on the mobile device.

The method contains a continuous analysis of said multiple training data and/or of said reworked measurement values and/or of said raw sensor values and/or of personal user data and/or of the further training data on said training data server; said continuous analyses being based on a training model; said training model being stored on said training data server and combining a first submodel and a second submodel; said training model containing said multiple training data and/or said reworked measurement values and/or said raw sensor values and/or said personal user data and/or said further training data as input data; said training model predicting the performance of said user in strength training on the basis of said first submodel; said training model controlling the strength training of a user on the basis of said second submodel.

In order to describe the performance of the user in strength training it is possible to use several measurement variables, for example one repetition maximum/concentric maximal strength, multiple repetition maximum, movement repetitions and training load, the time under tension of eccentric and concentric muscle length changes and isometric muscle contractions, forced per unit time, speed and/or angular speed, (local) fat-free muscle mass, impulse, physical effect, and these can serve as output of the training model on the basis of the first submodel. The terms "output", "output data" and "performance" of the user in the strength training are used synonymously. These measurement variables of the performance in strength training can relate to strength-training exercises and/or muscles and/or muscle groups and/or body segment movements. The training model can make the selection of a measurement variable of the performance in strength training dependent on the training method which is applied by the user and/or use the latter in combination. The training methods can be established on the basis of a subset of the multiple training data, for example on the basis of the number of movement repetitions and/or the time under tension and/or the training load. By way of example, it is possible to distinguish between the training methods of intramuscular coordination method, hypertrophy-specific method, mixed method, muscular endurance method or speed-oriented maximum strength method. By way of example, when applying the intramuscular coordination method, the "one repetition maximum" measurement variable lends itself since only a small number of movement repetitions are carried out with a high training load and the "one repetition maximum" describes the greatest training load which, despite the greatest possible effort, can only be moved once. In the case of hypertrophy-specific training, it may, for example, be the (local) fat-free muscle mass that is of interest, which, for example, can be measured by means of the other devices (e.g. a "body composition analyzer"—bioelectric impedance analysis). Data from other devices can, for example, be transmitted to the mobile device via the wireless interface or the interface and/or to the training data server via a computer so that these are available to the training model and the submodels. The measurement variables of the performance in strength training can be can combined to form a performance index or several performance indices in order to be able to provide the user with a simpler overview in respect of his current performance.

In order to measure the performance, it is possible to make a distinction between direct and indirect performance diagnostics. Direct performance diagnostics would provide a sport motor activity test method, which is carried out independently from the actual training process. By way of example, this could provide determining the isometric maximal strength on a force plate or measuring the one repetition maximum, which, for example, is carried out prior to and after a three-month training cycle. By contrast, indirect performance diagnostics are carried out during the training time. The invention contains an indirect approach to performance diagnostics in strength training, which extracts the implicitly obtained information of the performance at the time t from the multiple training data and/or the further training data and/or the reworked measurement values and/or the raw sensor values and/or the personal user data. As a result, additional test methods (e.g. carrying out test movements when measuring the one repetition maximum) are dispensed with and it is possible to acquire and monitor the performance continuously (in each training unit).

In order to ensure the reliability of the indirect measurement of the performance in strength training, knowledge about the level of exertion (also referred to as load termination criterion, level of exhaustion or level of maximum exertion) of the user in the respective training set is necessary. Theoretically, when relating to the performance, the assumption would always have to be made of a maximum load, in which the user is unable to continue the movement. Since a continuous maximum load cannot be presumed, different levels of exertion have to be acquired and weighted differently (e.g. supramaximal, point of current muscle failure, repetition maximum, subjectively very difficult, subjectively difficult, subjectively average, etc.). The percentage quantification of the load in respect of performance, i.e. the percentage distance from e.g. the subjective mean load to the actual maximum performance, can be undertaken on the basis of empirical values. The method contains establishing the level of exertion in a training set.

Furthermore, the latter can be put into a percentage ratio in relation to the performance. The acquisition can be undertaken based on, inter alia, the raw sensor values. For this, there are a multiplicity of algorithmic approaches from machine learning. It is possible to distinguish between supervised learning, unsupervised learning and reinforcement learning. By way of example, this can be undertaken by means of data-based modeling paradigms (e.g. artificial neural networks, hidden Markov models) and/or further mathematical/statistical methods. In the case of supervised learning, the user manually specifies to the mobile device with which level of exertion the training set was completed (so-called training data/learning data for a learning algorithm). As a result of the training data/learning data, the learning algorithm adapts itself independently and calculates itself with which level of exertion further training sets were carried out. Thereafter, the user can himself check whether the later calculations are correct (so-called validation data for the learning algorithm). The learning algorithm can contain a mixture of supervised, unsupervised and reinforcement learning and be carried out both on the mobile device itself and also on the training data server. Furthermore, an extra button designed specifically for this can, for example, be present on the mobile device, by means of which button it is conveniently specified after each training set the level of exertion with which the training set was completed. Acquiring the level of exertion can be complemented by a pulse measurement. By means of questioning via the user interface and/or display unit of the mobile device, it is possible to acquire the subjective current form of the user on the day of a training unit in order, for example, to apportion a lower weighting to bad performance values on that particular day.

Data-based modeling approaches, such as e.g. model trees or artificial neural networks, may lend themselves to predicting the performance of a user in strength training. Artificial neural networks are black box modeling, as a result of which it is subsequently hardly possible to make causal interpretations. In data mining, model trees were developed for numerical predictions, which are similar to the model structure of artificial neural networks. By contrast, model trees supply a repeatable and understandable representation by virtue of subdividing the induced function into linear sections, as a result of which additional training data analyses are made possible on the basis of the model tree. Artificial neural networks or the optimized model trees, which have previously not been used in strength training, are integrated in the first submodel and are combined with the second submodel in the training model. On the basis of the first submodel, the training model can image the interaction between training load (input of the training model) and performance (output of the training model) in the strength training process with several attributes, i.e. for example several load parameters (scope of training, training duration, training intensity, training frequency, ratio between activity and training duration) and, as a result, it is possible to analyze training effects (modified performance values) and, as a result, predict these. Here, the first submodel is not only bound to the described input data and/or output data and it is also possible to complement and/or replace these with further measurement variables. In order to improve the model quality, it is also possible to apply further approaches from data mining and/or machine learning and/or statistics and/or other mathematical and/or computer-scientific approaches.

Fuzzy logic, which was not previously used in strength training, lends itself to controlling the strength training. Integrated into the second submodel is a knowledge-based fuzzy model and state transition modeling in the form of a finite automaton for algorithmic control of the strength training, resulting in specific training recommendations for the user. Within the second submodel, the user is subdivided into so-called fields of applications (e.g. children, adolescents, health fitness, prevention, rehabilitation, beginner athlete, advanced athlete) on the basis of fuzzy functions and the personal user data. A large number of empirical research results into strength training, which, for example, are described in literature relating to sports sciences serves as a basis for functions and rules of the second submodel. By means of functions and on the basis of rules (e.g. if-then rules), it is thus possible, for example, to calculate the necessary changes to a new training method, which, for example, was carried out after specific temporal training duration with a specific scope of training, a specific training intensity, ratio between activity and training duration and training frequency. Within the second submodel, process states in the strength training process are diagnosed for this; state changes are modeled (e.g. change of training methods or strength-training exercises) and a finite automaton (state transition model) controls this process. The control can occur on different training process planes (temporal depth of the control, e.g. movement repetition, training set, strength-training exercise, training unit, micro-cycle, meso-cycle, macro-cycle etc.). Furthermore, information of said interaction between training load (input of the training model) and performance (output of the training model) in the strength training process, in the first submodel, can be combined with the control of the second submodel, in the training model. Here, the control of the second submodel relates both on the load parameters to be selected by the user and to the strength-training exercises, the selection, sequence and form of organization of which are made depending on the multiple training data and/or the further training data and/or the reworked measurement values and/or the raw sensor values and/or the personal user data. Here, inter alia, the most important contraindications when recommending load configurations and strength-training exercises are taken into account on the basis of the personal user data. This control is generally undertaken by the external user (e.g. trainer), who, for example, receives these on his computer as action recommendation.

BRIEF DESCRIPTION OF THE FIGURES

In the following text, the invention will be explained in more detail on the basis of figures. In detail:

FIG. 6 shows a "biceps curl" strength-training exercise using the "barbell" training utensil carried out by a standing user in an exemplary manner;

FIG. 7 shows a "bench press" strength-training exercise using the "barbell" training utensil carried out by a lying user in an exemplary manner, with view from behind on the user;

FIG. 12 shows an exemplary angled middling forearm position of the "biceps curl" strength-training exercise using the "dumbbell" training utensil.

FIG. 1 shows an overview in the form of a block diagram of an embodiment variant of the arrangement according to the invention. In FIG. 1, a mobile device 1 is, in an exemplary manner, attached to the wrist/forearm 39 (FIG. 5) of a user 2. Further possible options of the body segment attachment are depicted in FIG. 5. The mobile device 1 contains a user interface 3, for example in the form of keys/buttons. A display unit 4 shows the user 2 a graphical user interface 7 and can itself be embodied as a user interface. A second storage unit 5 contains predetermined movement data, consisting of the characteristic variables of set movement patterns of N strength-training exercises using a training utensil Y. The mobile device 1 contains an accelerometer 6a, a rate sensor (gyroscope) 6b and a magnetometer 6c. A processor 13 inter alia recalls the predetermined movement data from the second storage unit 5 and obtains raw sensor values from the sensors 6a and/or 6b and/or 6c. Reworked measurement values are generated in the algorithm 8 depending on the raw sensor values and the predetermined movement data from the second storage unit 5. Multiple training data are calculated precisely on the basis of the reworked measurement values.

A strength-training exercise and/or a training utensil, for example a barbell 11, and/or a training load can be selected by means of an RFID unit 9 and an RFID tag 10. FIG. 3 shows an exemplary arrangement of the RFID tag on the weights of a weight stack 31 of a "cable machine" or "machine" training utensil. Communication with external devices 12, for example turnstiles and/or lockers and/or base stations in fitness studios, can take place via the RFID unit 9.

Figure 1:
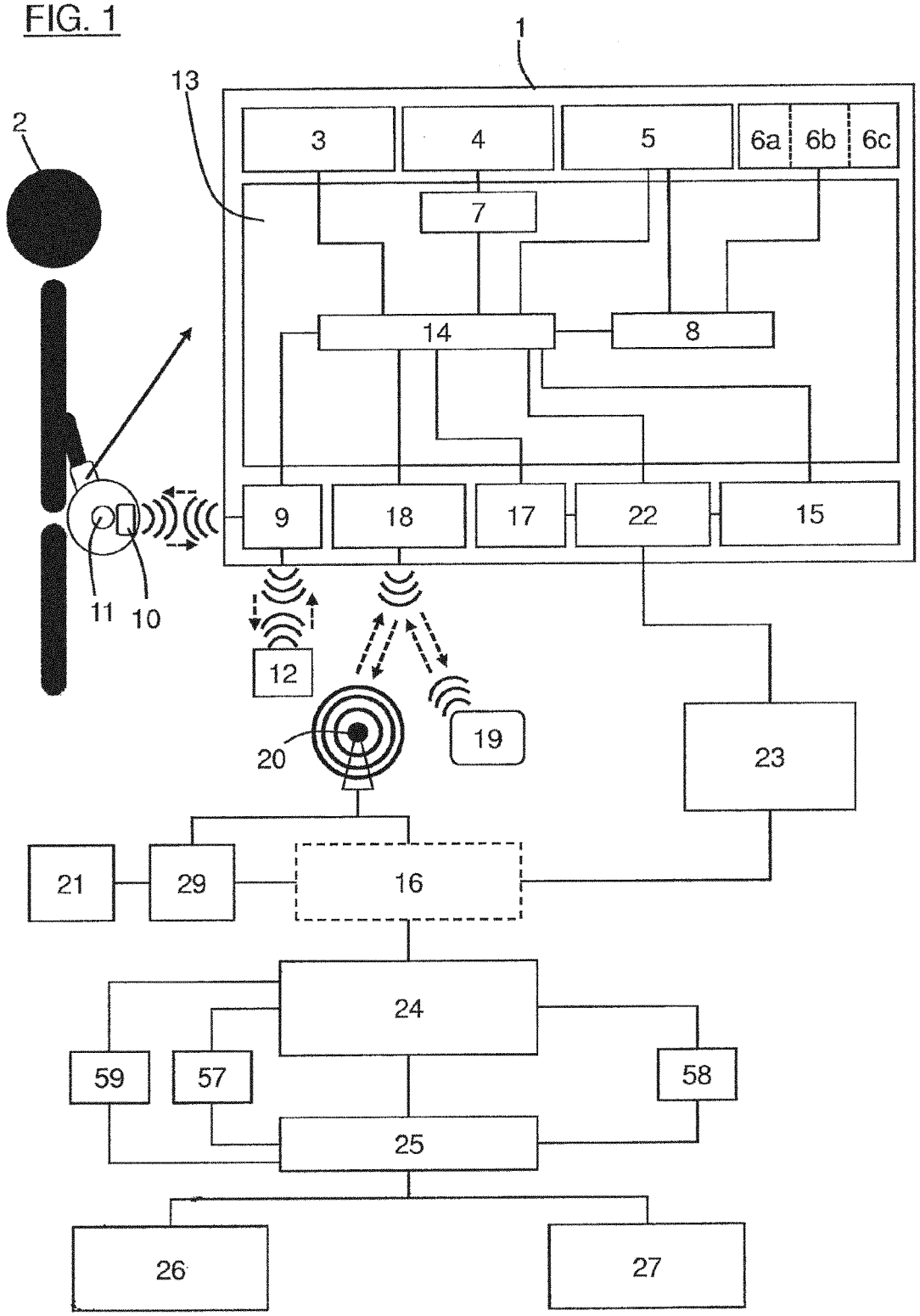
FIG. 1 shows an overview in the form of a block diagram of one embodiment variant of the arrangement according to the invention.

In the system 14 (FIG. 1), the multiple training data and/or raw sensor values and/or reworked measurement values and/or further training data are brought to a display unit 4 via the graphical user interface 7 and/or stored in a first storage unit 15. The system 14 furthermore manages the RFID unit 9, wireless interface 18 and interface 22 components. The system 14 organizes the storage units 5 and 15, the energy budget of the equipment and the processing of user inputs. The system 14 monitors the charge state of a rechargeable battery 17 in order to relay appropriate notifications to the user 2 in the case of low-voltage. The interface 22 (also referred to as data interface) is employed for both the data transmission and the power supply of the mobile device 1. The interface 22 (FIG. 1) enables data transmission to a computer 23 of the user 2, for example by USB. The computer 23 can transmit the multiple training data and/or the reworked measurement values and/or the raw sensor values and/or the further training data to a training data server 24 via the Internet 16. An external user 21 can access the training data server 24 via a computer 29 and via the Internet 16. The wireless interface 18 serves for the wireless transmission of data. A sensor module 19, which for example corresponds to a restricted embodiment variant of the mobile device 1, without user interface 3, display unit 4 and RFID unit 9, enables the acquisition of additional raw sensor values and the wireless transmission of the additional raw sensor values to the mobile device 1.

Figure 2:
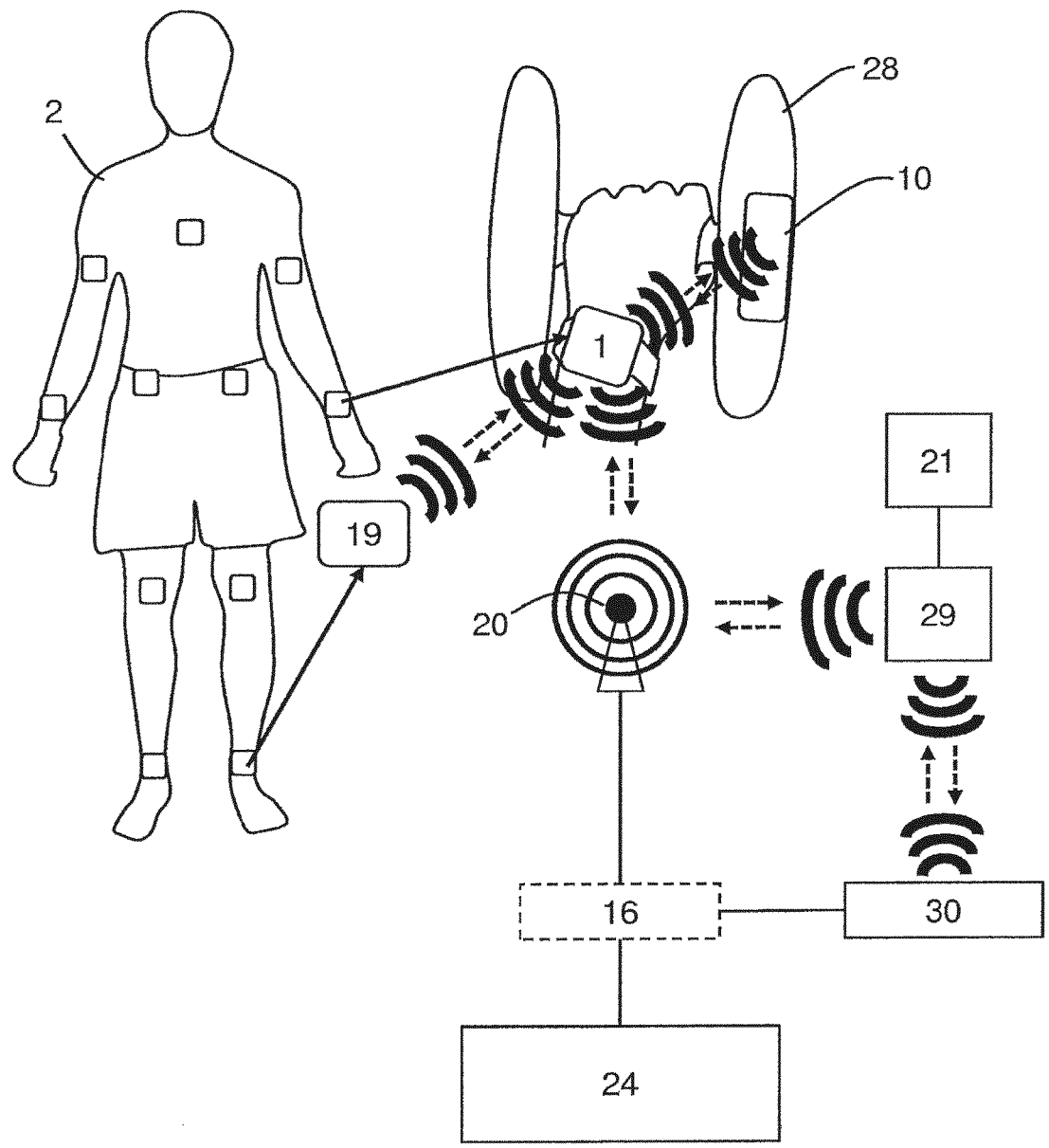
FIG. 2 shows a further overview of an embodiment variant of the arrangement according to the invention.

FIG. 2 shows a further overview of an embodiment variant of the arrangement according to the invention. In FIG. 2, the mobile device 1 is attached to the wrist/forearm 39 (FIG. 5), embodied in the form of a wristwatch and responsible for acquiring arm and upper body movements. By way of example, the sensor module 19 is attached to the high ankle 41 (FIG. 5), responsible for acquiring leg movements and can optionally be repositioned on the wrist 39, thigh 40 (above the knee), hip 38, upper arm 37 and chest 36 body segments. The wrist/forearm 39, thigh 40, high ankle 41, hip 38, upper arm 37 and chest 36 body segments are depicted in a large view in FIG. 5. In the strength-training exercises, in which pure wrist extensions and bends are carried out, the sensor module can be attached directly on the training utensil (not depicted). The wireless interface 18 (FIG. 1) is configured to transmit data to a wireless station 20. This wireless station 20 serves for data transmission to an external user 21 and/or for data transmission to a training data server 24 via the Internet 16. This data transmission can be undertaken both directly, via a connection to a computer 29, and also indirectly, via the Internet 16 and the training data server 24. This data transmission can be brought about in both wired and wireless fashion. A wireless data transmission can be undertaken by means of an interface 30 (FIG. 2), for example a WLAN router, which, for example, is placed in a fitness studio. By way of example, the external user 21 can receive the multiple training data and/or the reworked measurement values and/or the raw sensor values and/or further training data from the mobile device 1 in real-time in the training area in the fitness studio, by means of computer 29 (e.g. a mobile tablet PC).

Situated on the training data server 24 is a training model 25, which combines a first submodel 26 and a second submodel 27 and thereby implicates the analysis of strength training. As input data 57, the training model 25 obtains the multiple training data and/or the reworked measurement values and/or the personal user data and/or the further training data and/or the raw sensor values. On the basis of the first submodel 26, the training model 25 is configured to predict the performance 59 of the user 2 in strength training. The terms "output", "output data" and "performance" of the user in strength training are used synonymously and are described by 59. On the basis of the first submodel 26, several measurement variables for describing the performance 59 of the user 2 in strength training can be used as output 59 of the training model. On the basis of the second submodel 27, the training model 25 is configured to control 58 the strength training of the user 2, i.e. to generate training recommendations.

Figure 4:
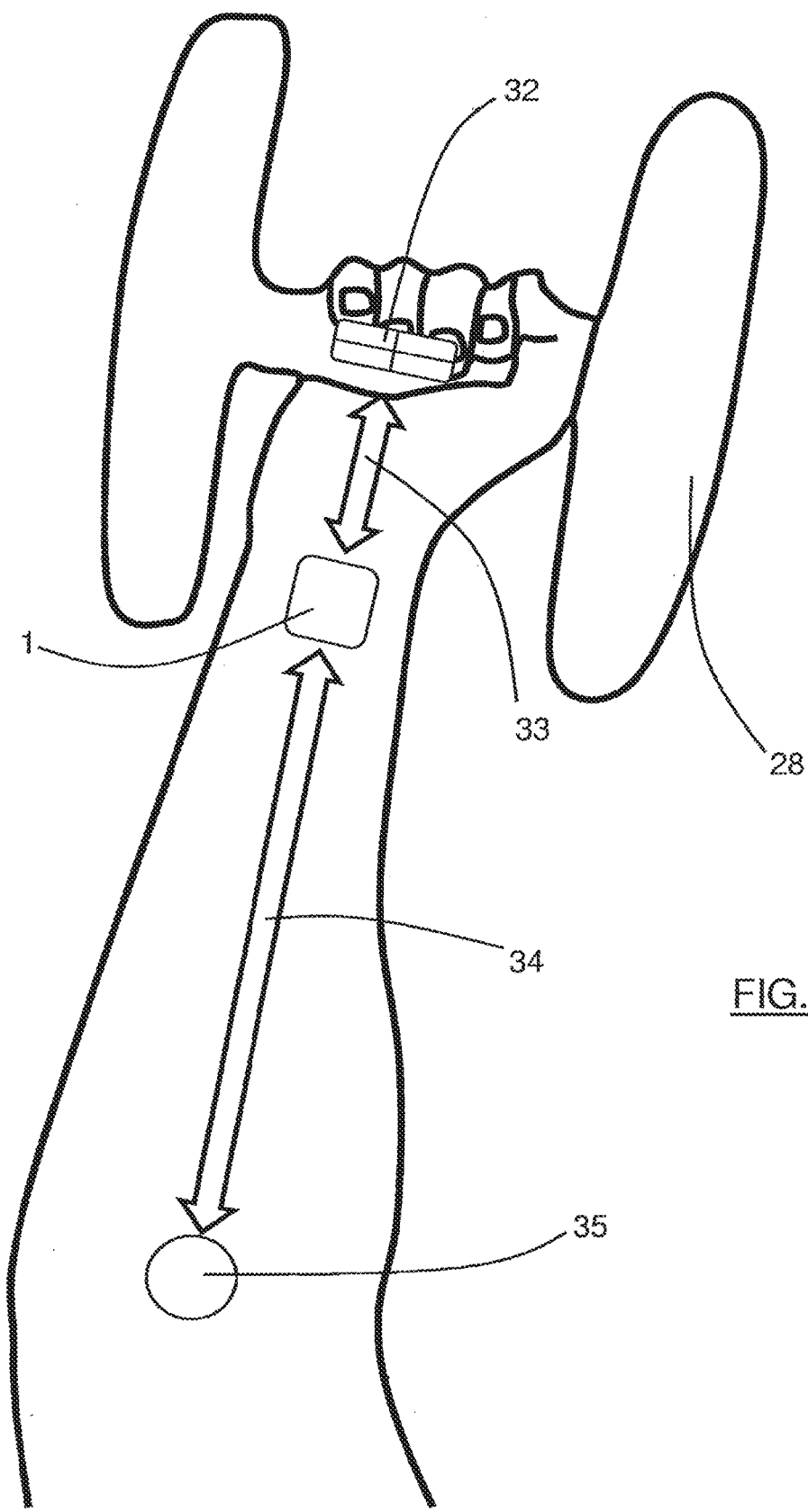
FIG. 4 shows a mobile device on a body segment with the distance to the force contact point of the training load and the distance to the rotational axis (elbow joint)

The following embodiments will be described on the basis of FIG. 4. In order to calculate the torque, the force and the distances 33 and 34 have to be known. Accordingly, it is necessary, once, to manually enter into the mobile device 1 the distance 33 of the mobile device 1 from the force contact point of the training load 32 and the distance 34 of the mobile device from the rotational axis (elbow joint) 35. The dimensions of the mobile device 1 have already been provided.

Figure 3:
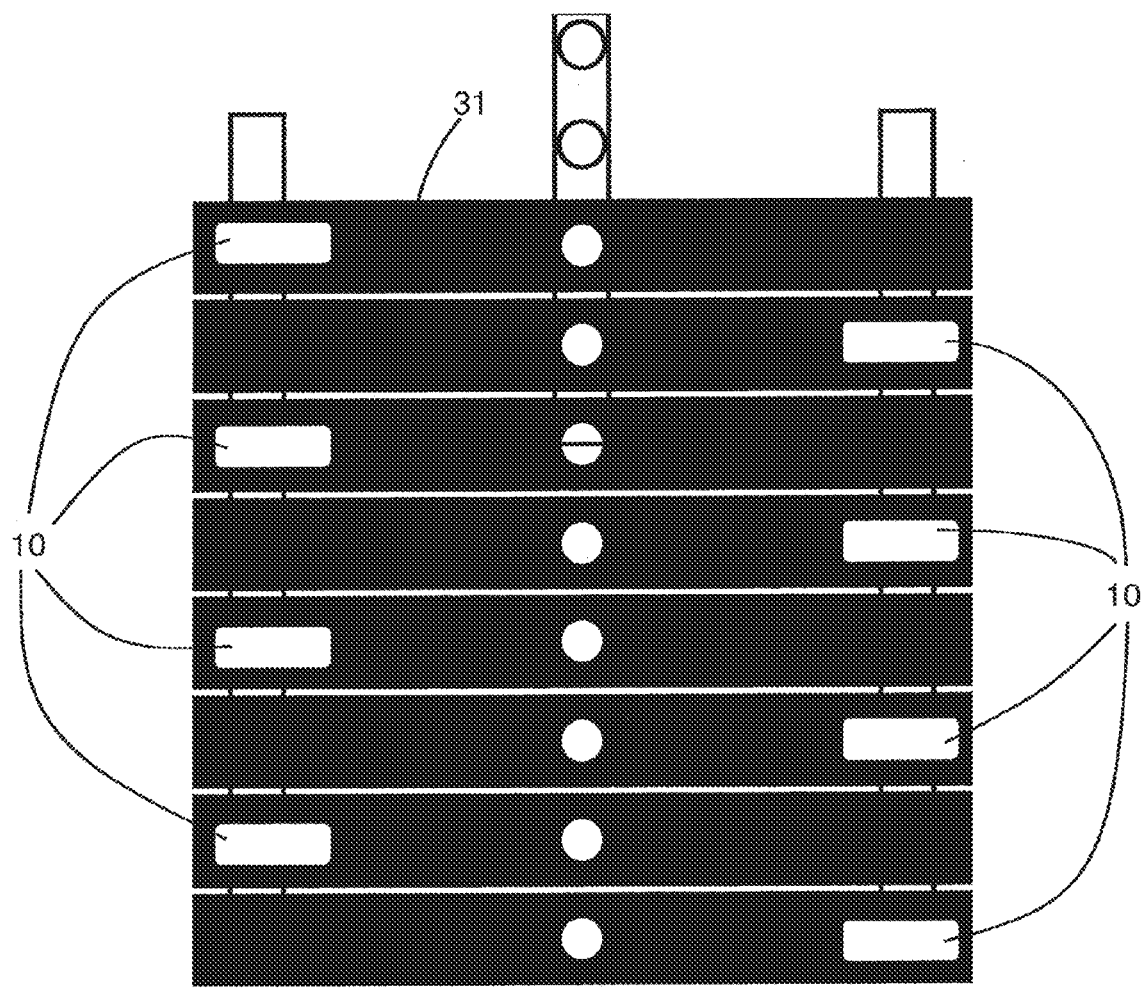
FIG. 3 shows an exemplary arrangement of RFID tags on the weight stack of the "machine/equipment" and/or "cable machine" training utensils.
Figure 5:
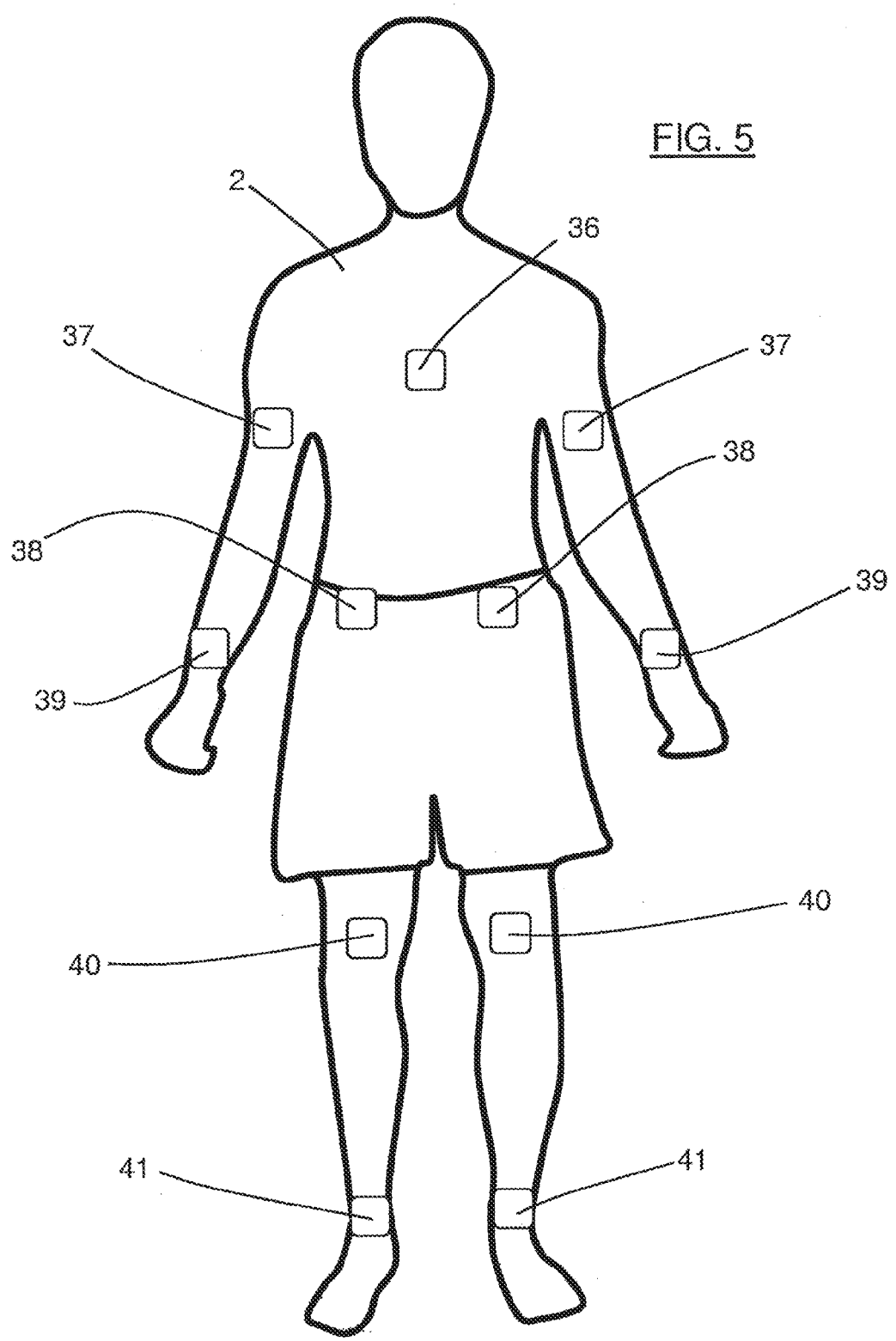
FIG. 5 shows a standing user with the body segment regions, on which a mobile device and/or a sensor module can at least be attached.

FIG. 6 shows the "biceps curl" strength-training exercise from the side view. FIG. 6 is subdivided into sub-figures a) to e), which show a sequence of times of several movements and represent the same elements. In FIG. 6, sub-figure a), 43 shows a forearm of the user 2. 11 shows the "barbell" training utensil. 42 shows the muscle "m. biceps brachii" in a stretched initial position. The mobile device 1 is attached to the forearm/wrist 39 (FIG. 5). If the user 2 in FIG. 6, sub-figure b) lifts the forearm 43, the mobile device 1 moves with the forearm 43 and the training utensil 11 covers the path 45 from the initial position 44. The muscle 42 has performed dynamic-positive muscle work, required a certain amount of time for this concentric muscle length change and is situated in a middling position. A partial movement was carried out, which was not carried out over the full movement amplitude or range of motion (abbreviated ROM). The mobile device 1 calculates the path 45 covered and the displacement/time profile of the force contact point of the training load of the training utensil 11, the time under tension of concentric muscle length changes of the target muscle system "m. biceps brachii" 42, of the supporting muscles and the stabilizing muscles, and the rotational work from torque and rotational angle. Sub-figure c) in FIG. 3 shows that the muscle 42 performs dynamic-negative muscle work and that the training utensil 11 is lowered.

In FIG. 6, sub-figure d), 42 shows a muscle that has completely contracted as a result of lifting the training utensil 11. The forearm cannot be brought any closer to the upper arm. The full movement amplitude was utilized. In FIG. 6, sub-figure d), 46 shows a random deviation of the path profile of the training utensil from the ideal line of the movement, which results in a longer path covered and which is acquired by the mobile device 1. In FIG. 6, sub-figure e), 47 shows a displacement/time profile of the training utensil, in which the movement was stopped in the middle of the movement amplitude. When statically holding the training utensil, no work is carried out in the physical sense, but energy is continued to be consumed in the muscle. More energy is also consumed in the case where a longer path 46 covered. Thus, it does not suffice to calculate the scope of the training purely by the mechanical work, which is why the measurement variable "time under tension" is added. 48 shows the axes in which the mobile device 1 can calculate the displacement/time profile.

Figure 8:
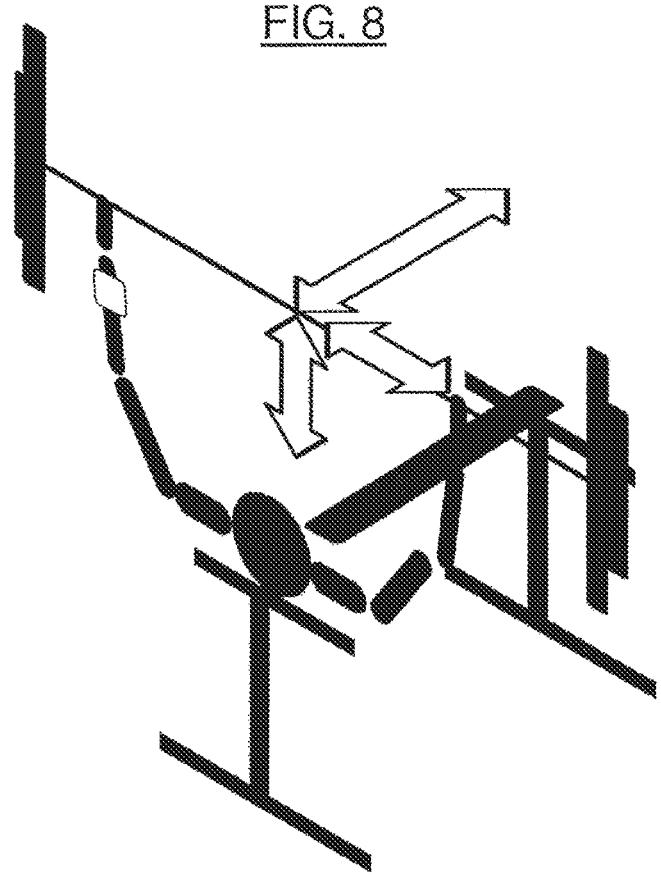
FIG. 8 shows a three-dimensional perspective of the "bench press" strength-training exercise.

FIG. 7 shows the multi-joint "bench press" strength-training exercise from a rear view. For better illustration purposes, FIG. 8 shows the bench press strength-training exercise in a 3D-perspective view. FIG. 7 is subdivided into sub-figures a) and b), which show a sequence of times of a movement and represent the same elements. In FIG. 7, sub-figure a), 11 shows the "barbell" training utensil, which is held statically by the user 2 in an initial position. 49 shows a grip width of the user 2 on the training utensil 11. The mobile device 1 is attached to the wrist/forearm 39 (FIG. 5) of the user 2. As soon as the user 2 lowers the training utensil 11 in FIG. 7, sub-figure b), the mobile device 1 acquires this movement and calculates the displacement/time profile along at least one of the three axes 48. As is possible to identify from the initial position of the mobile device 1 in FIG. 7, sub-figure a), to the end position in FIG. 7, sub-figure b), of the mobile device 1, a small portion of rotational movement is created, which would be interpreted incorrectly by a pure accelerometer. In this example, there still are relatively low centrifugal forces. However, the greater the distance from the rotational axis becomes, the greater the centrifugal forces become in the case of rotational movements (for example FIG. 6: "biceps curl"). Furthermore, the further said multiple training data are calculated.

Figure 10:
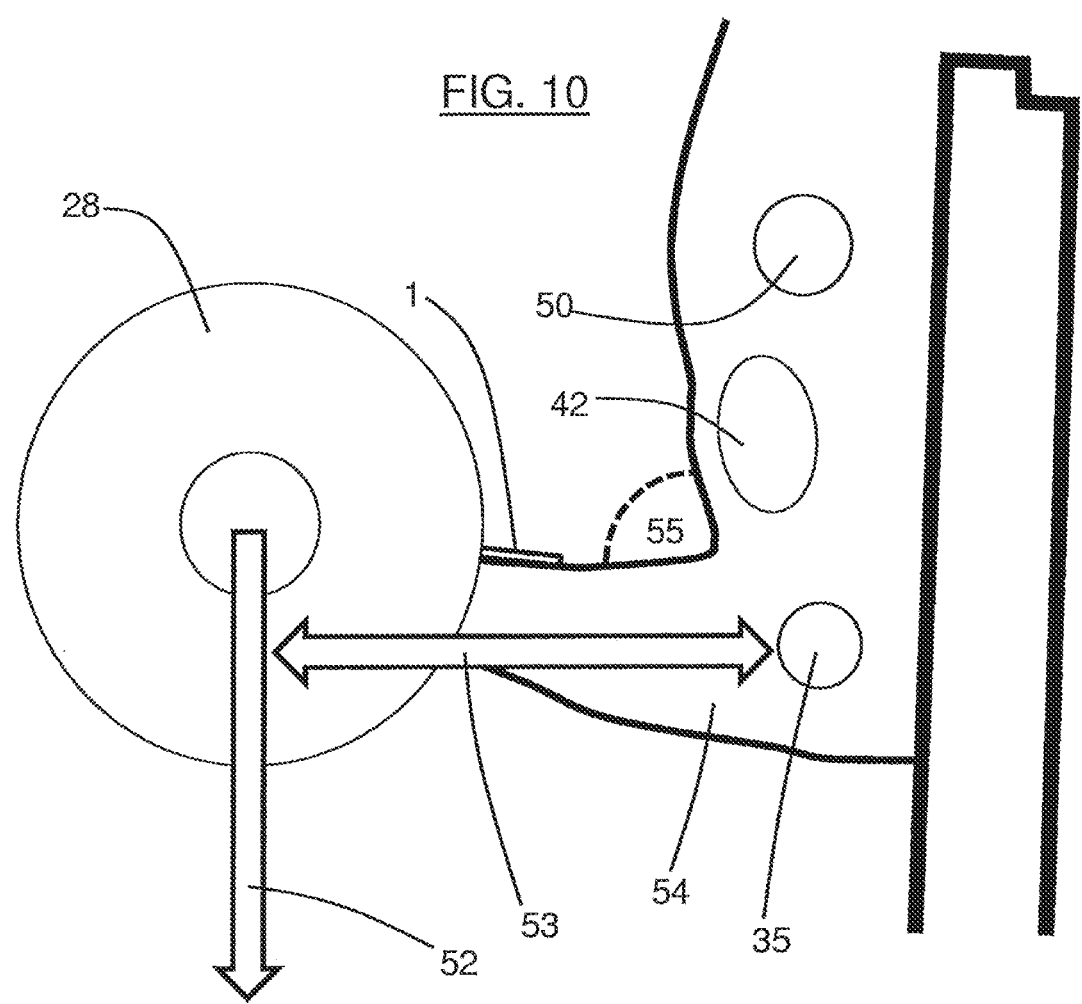
FIG. 10 shows an exemplary middling forearm position in the "biceps curl" strength-training exercise using the "dumbbell" training utensil, perpendicular to the ground.

What emerges in respect of the lever and joint angle conditions of the "biceps curl" strength-training exercise in FIG. 10 is that the line of action of the force 52 moves closer to the rotational axis/joint 35 (not explicitly depicted in FIG. 10) if the angle between forearm and upper arm 55 of the joint 35 becomes too large or too small, as a result of which a lower torque is generated in the case of an unchanging force. An optimum work angle emerges, at which a maximum distance 53 of the line of action 52 of the force contact point of the training load 32 (FIG. 4) is generated from the rotational axis/joint 35 and hence a greater torque is generated in the case of an unchanging force. The user can be supported in maintaining the optimum work angle by optical and/or acoustic and/or haptic signals of the mobile device 1.

Figure 9:
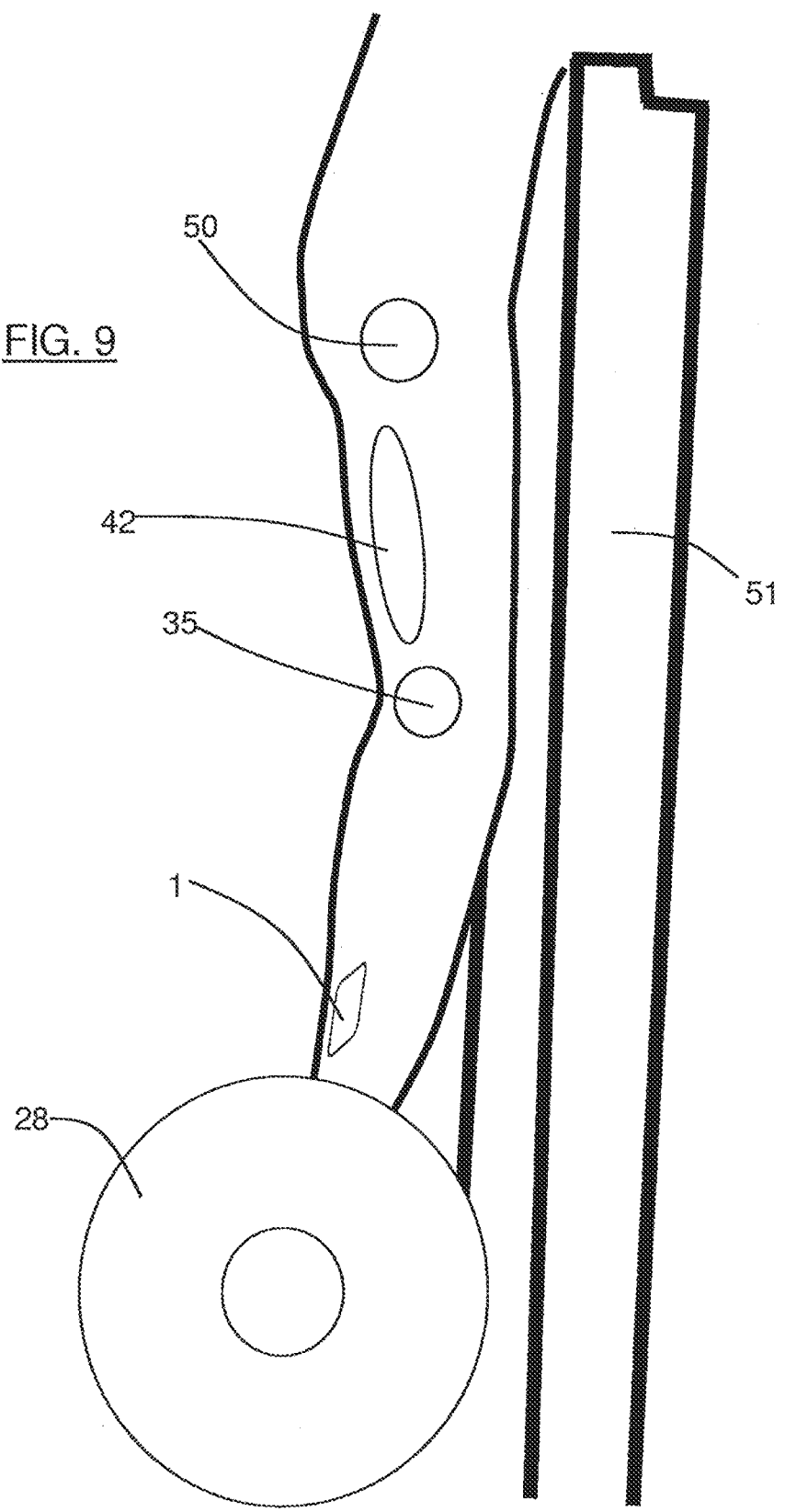
FIG. 9 shows an exemplary initial position of the "biceps curl" strength-training exercise using the "dumbbell" training utensil, perpendicular to the ground.

FIG. 9 shows the initial position of the "biceps curl" strength-training exercise. The mobile device 1 is attached to the forearm/wrist 39 (FIG. 5). 35 shows the rotational axis, i.e. the elbow joint, and 42 shows the target muscle "m. biceps brachii" in its initial length. The position of the armrest 51 and that of the arm are completely perpendicular. The joint that is responsible for the position is the shoulder joint 50. 28 shows the "dumbbell" training utensil. In FIG. 10, 1 depicts the mobile device, and FIG. 10 also depicts the position of the forearm 54 (lever), in which the distance 53 of the line of action 52 of the force contact point of the training load 32 (FIG. 4) is greatest from the rotational axis/elbow joint 35. In this perpendicular arm position of the shoulder joint 50, the target muscle "m. biceps brachii" 42 is situated in a middling length state. Thus, in FIG. 10, the greatest torque (said optimum work angle) and hence the greatest amount of rotational work are brought about in a middling muscle length state. 28 shows the "dumbbell" training utensil.

Figure 11:
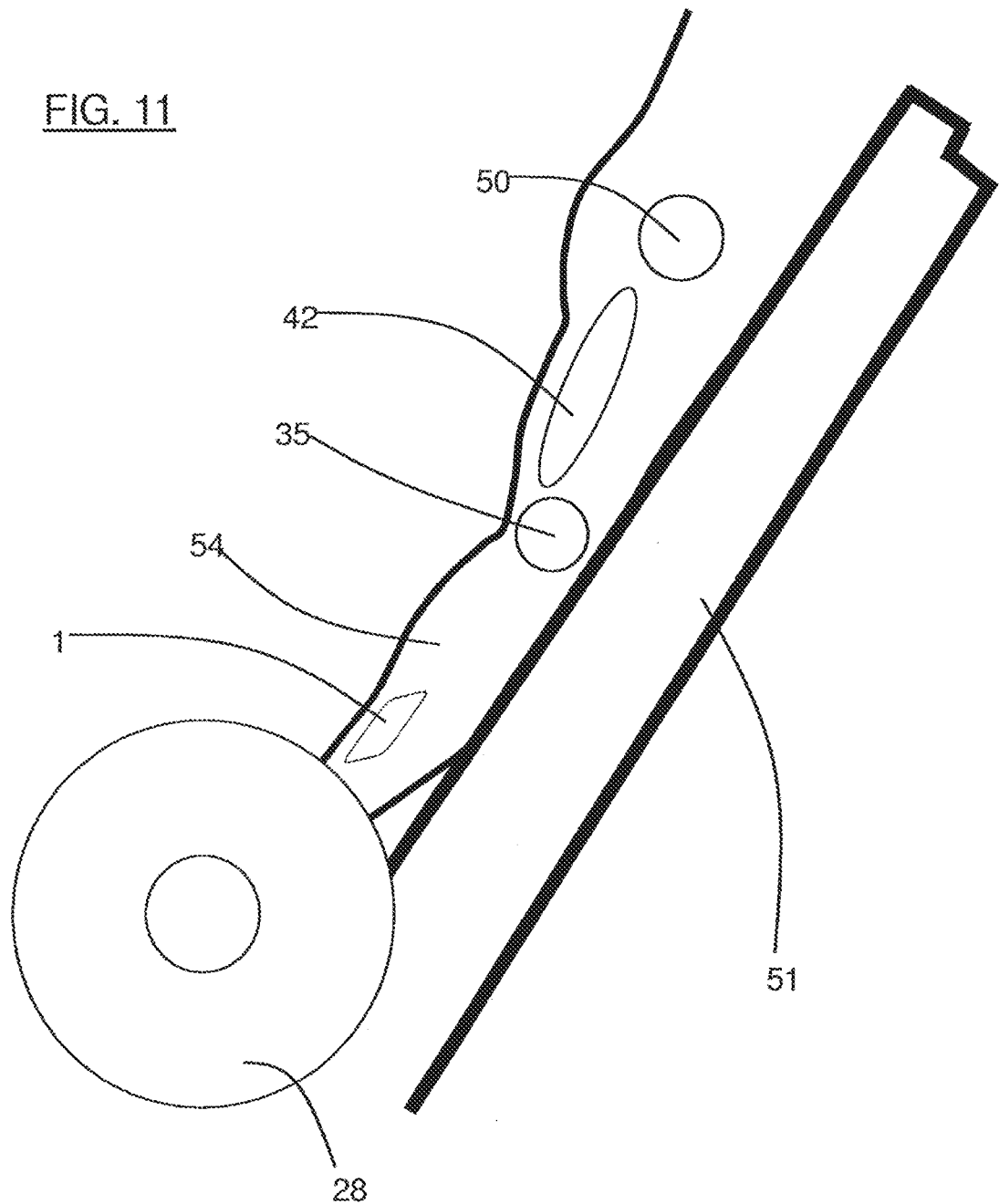
FIG. 11 shows an exemplary angled initial position of the "biceps curl" strength-training exercise using the "dumbbell" training utensil.

If one moves on to FIG. 11, an angled initial position of the armrest 51 and of the shoulder joint 50 is shown, i.e. not a perpendicular initial joint angle of the superior joint (shoulder joint) 50 in relation to the rotational axis/elbow joint 35. This initial angle of the complete arm or of the shoulder joint 50 can vary from strength-training exercise to strength-training exercise and from armrest to armrest. This initial angle can naturally be transferred to strength-training exercises with e.g. leg or upper body movements. By way of example, in the case of the "lying lateral raises" strength-training exercise with the "dumbbell" training utensil (not depicted), the initial angle of the whole human body has to be calculated, regardless of whether it lies horizontally to the ground on the training bench or whether the training bench was angled. Furthermore, 1 describes the mobile device, 54 describes the forearm, 35 describes the rotational axis/elbow joint, 42 describes the target muscle "m. biceps brachii" in its initial length and 28 describes the "dumbbell" training utensil.

In FIG. 12, 1 depicts the mobile device, and FIG. 12 also depicts the position of the forearm 54 (lever), in which the distance 53 of the line of action 52 of the force contact point of the training load 32 (FIG. 4) is greatest from the rotational axis 35. In this angled position of the armrest 51 or of the shoulder joint 50, the target muscle "m. biceps brachii" 42 is situated in a stretched length state. Thus, in FIG. 12, the greatest torque (said optimum work angle) and hence the greatest amount of rotational work are brought about in a stretched muscle length state.

On the basis of the descriptions in relation to FIGS. 9, 10, 11 and 12, it becomes clear that the initial angle of the superior joint (in the examples the shoulder joint or the armrest) is of importance for the length state of the target muscle, in which the greatest torque is generated. The mobile device 1 is configured to calculate the initial angle of the superior joint, in these examples on the basis of the shoulder joint 50 or the armrest 51, at the start of the movement, to calculate the torque and the length state of the muscular system in addition to said rotational work and to calculate said time under tension of eccentric and concentric muscle length changes and/or isometric contractions. FIGS. 9 to 12 show a single-joint (isolated/rotational) strength-training exercise. In the case of multi-joint strength-training exercises (straight line/translational movements—e.g. "bench press" in FIG. 7), the torque in a joint, for example in the case of upper body exercises, is dependent on the grip width 49 or, for example in the case of leg exercises, on the position of the feet.

The invention claimed is:

1. A method for mobile acquisition of training data, the method comprising:
    affixing a mobile device to a body segment;
    determining sensor values in movement patterns via said mobile device;
    calculating training data from said sensor values using said mobile device;
    storing said training data in a first storage unit in said mobile device;
    transmitting said training data from said mobile device to a computer via a data interface;
    selecting a strength-training exercise X with a set movement pattern and a training utensil Y, from strength-training exercises and training utensils via the mobile device;
    recalling predetermined movement data, consisting of characteristic variables of set movement patterns of said strength-training exercise X using said training utensil Y from a second storage unit in said mobile device;
    determining raw sensor values using said mobile device in said set movement patterns of said strength-training exercise X using said training utensil Y, consisting of acceleration and angular speed values;
    calculating reworked-measurement values via said mobile device based on said predetermined movement data and said raw sensor;
    calculating multiple training data using said mobile device, on the basis of said reworked measurement values.

2. The method as claimed in claim 1, wherein said calculation of reworked measurement values using said mobile device comprises at least one of the following steps:
    initially calibrating said mobile device in order to at least one of: improve said calculation and extend said multiple training data;
    including a magnetic flux density vector in said raw sensor values;
    fusing said raw sensor values with said predetermined movement data;
    integrating said acceleration values twice;
    filtering sensor offsets.

3. The method as claimed in claim 1, wherein said multiple training data, which are based on said raw sensor values, contain at least one of the following items of information:
    displacement/time profile of a force contact point of a training load along at least one of: the X-axis, Y-axis and Z-axis;
    at least one of: time under tension of eccentric muscle length changes, concentric muscle length changes, and isometric muscle contractions;
    number of movement repetitions;
    mechanical work;
    rotational work;
    muscle load;
    torque;
    force;
    impulse;
    physical effect;
    grip width;
    grip variant;
    foot position;
    initial angle of a superior joint;
    muscle length state;
    level of exertion;
    type of movement in a joint;

intensity technique applied in a training set;
training method.

4. The method of claim 1, wherein a user selects at least one of a training load, said training utensil, and said strength-training exercise in at least one of: (i) an automated manner by means of an RFID unit and RFID tag, and (ii) a manual manner by means of at least one of a user interface and display unit.

5. The method of claim 1, wherein said strength-training exercise is acquired automatically, proceeding from said raw sensor values.

6. The method of claim 1, wherein additional raw sensor values are transmitted from at least one sensor module to said mobile device via a wireless interface.

7. The method as claimed in claim 1, wherein at least one of said multiple training data, said reworked measurement values, said raw sensor values, and further training data are transmitted to at least one of: (i) the first storage unit in said mobile device, (ii) the computer, and (iii) a wireless station via at least one of an interface and the wireless interface; and transmitted to at least one of (a) a training data server via the Internet, and (b) a computer of an external user via at least one of the Internet and direct connection.

8. The method as claimed in claim 7, wherein there are continuous analyses of at least one of: said multiple training data, said reworked measurement values, and raw sensor values, personal user data, and said further training data on said training data server;
said continuous analyses are based on a training model;
said training model is stored on said training data server and combines a first submodel and second submodel;
said training model contains at least one of: said multiple training at, said reworked measurement values, and raw sensor values, said personal user data, and said further training data as input data;
said training model predicts the performance of said user in strength training on the basis of said first submodel;
said training model controls the strength training of said user on the basis of said second submodel.

9. The method of claim 1, wherein a level of exertion in a training set is acquired.

10. The method of claim 1, wherein at least one of optical, acoustic, and haptic signals are provided to said user via said mobile device for purposes of support when carrying out the predetermined movement patterns.

11. The method of claim 10, wherein said signals contain information about at least one of a rhythm, an amplitude, and the direction of the predetermined movement patterns.

12. The method as claimed in claim 1, wherein said calculation of reworked measurement values using said mobile device comprises fusing said raw sensor values with said predetermined movement data.

13. The method of claim 1, wherein the reworked measurement values are generated in an algorithm based on said raw sensor values and said predetermined movement data from the second storage unit.

14. A device for mobile training data acquisition, the device comprising:
a housing;
a sensor for determine sensor values:
a processor for calculating training data;
a first storage unit for storing said training data;
a data interface for transmitting said training data to a computer;
a second storage unit on which predetermined movement data are stored, wherein the predetermined movement data consist of characteristic variables of set movement patterns of strength-training exercises using a training utensil Y, and wherein the predetermined movement data is configured to be recalled from the processor;
an accelerometer and rate sensor configured to determine at least one of acceleration and angular speed values, which are configured to be transmitted to the processor.

15. The device of claim 14, wherein the device is a wristwatch.

16. The device of claim 14, wherein the device contains a wireless interface for wireless data interchange with at least one of: (i) at least one sensor module, (ii) at least one wireless station, and (iii) any other devices.

17. The device of claim 14, wherein the device contains an RFID unit, which is embodied as RFID unit and as RFID transmission unit;
said RFID unit is configured to communicate with RFID tags, which are (i) attached to said training utensil, (ii) integrated in said training utensil, and/or (iii) situated in the vicinity of at least one of said training utensil and external devices.

18. The device of claim 14, wherein the device contains a magnetometer for measuring magnetic flux density vector.

19. The device of claim 14, wherein the device contains at least one of a user interface, a display unit, a vibration motor, and a loudspeaker.

* * * * *